United States Patent [19]

Smith et al.

[11] Patent Number: 5,283,188

[45] Date of Patent: * Feb. 1, 1994

[54] ISOLATION, PURIFICATION, CHARACTERIZATION, CLONING AND SEQUENCING OF N$^\alpha$-ACETYLTRANSFERASE

[75] Inventors: John A. Smith, Brookline; Fang-Jen S. Lee, Somerville, both of Mass.

[73] Assignee: The General Hospital Corporation, Boston, Mass.

[*] Notice: The portion of the term of this patent subsequent to Jul. 7, 2009 has been disclaimed.

[21] Appl. No.: 863,023

[22] Filed: Apr. 3, 1992

Related U.S. Application Data

[60] Division of Ser. No. 533,353, Jun. 5, 1990, Pat. No. 5,128,459, which is a division of Ser. No. 284,344, Dec. 14, 1988, Pat. No. 4,966,848, which is a continuation-in-part of Ser. No. 153,361, Feb. 8, 1988, abandoned.

[51] Int. Cl.$^5$ .................... C12N 9/10; C12N 15/55; C12N 15/74; C12N 15/79

[52] U.S. Cl. .................... 435/193; 435/69.1; 435/252.3; 435/252.31; 435/320.1; 536/23.2; 935/14; 935/28; 935/29; 935/34; 935/39; 935/68; 935/74

[58] Field of Search .................... 435/193, 69.1, 252.3, 435/252.31, 320.1; 536/27, 23.2

[56] References Cited

U.S. PATENT DOCUMENTS 4,966,848 10/1990 Smith et al. .................... 435/193
5,128,459 7/1992 Smith et al. .................... 536/27

*Primary Examiner*—Robert A. Wax
*Assistant Examiner*—William W. Moore
*Attorney, Agent, or Firm*—Sterne, Kessler, Goldstein & Fox

[57] ABSTRACT

This invention is directed to N$^\alpha$-acetyltransferase with a molecular weight of about 180,000 daltons, said N$^\alpha$-acetyltransferase being composed of two subunit peptides having molecular weights of about 95,000 each, having enzyme activity greater than 100 wherein one unit of activity is defined as 1 pmol of acetyl residues incorporated into adrenocorticotropic hormone (ACTH) (amino acids 1-24) under standard assay conditions. This invention is further directed to a method for purifying the N$^\alpha$-acetyltransferase.

28 Claims, 17 Drawing Sheets

A

Sequence data

```
                      K   I   E   G   A   S   A   S   P   I   C   C   H   V   L   G   I   Y   M
Peptide 27-3
Probe N1       3'-TTC TAA CTT CCA CGA AGA CGA AGG GGT TAG ACG ACG GTG CGA AAC CCA TAG ATG TAC-5'
                                    *       *           *           *       **      *
                      S   V   A   A   Y   P   S   D   Q   D   N   D   V   F   G   E
Peptide 11-3-2
Probe N2       3'-AGA CAA CGA CGA ATG GGT AGA CTG GTT CTG TTG CTG CAA AAG CCA CTT-5'
                 **                      **      *       *       *
```

```
5'.....TTTCCAGGACCCTAACGAAGT
 22  ATG TCT AGG AAA AGA AGT ACT AAG CCC AAG CCA GCA GCT AAA ATA GCT TTG AAA AAA GAA AAT GAC CAG
  1   M   S   R   K   R   S   T   K   P   K   P   A   A   K   I   A   L   K   K   E   N   D   Q

91  TTC CTC GAG GCA TTG AAA CTA TAC GAA GGG AAG CAA TAC AAA AAA TCT CTC AAG CTG CTA GAC GCA ATT
 24   F   L   E   A   L   K   L   Y   E   G   K   Q   Y   K   K   S   L   K   L   L   D   A   I

160  TTG AAA AAA GAC GCT AGT GGT AGT CAC GTT GAT TCC CTT GAT TTA TAT TCT GTA GGT GAG
 47   L   K   K   D   A   S   G   S   H   V   D   S   L   D   L   Y   S   V   G   E

229  AAA GAT GAC GCT GCT TCC TAC GTG GCT AAT GCC ATC AGA AAA ATT GAA GGC GCT TCA GCA TCA CCA ATC
 70   K   D   D   A   A   S   Y   V   A   N   A   I   R   K   I   E   G   A   S   A   S   P   I

298  TGC TGT CAT GTA TTA GGT ATC TAC ATG AGA AAC ACC AAA GAG TAC AAA GAA TCT ATT AAA TGG TTC ACG
 93   C   C   H   V   L   G   I   Y   M   R   N   T   K   E   Y   K   E   S   I   K   W   F   T

367  GCA GCT TTG AAC AAT GGG TCC ACT AAC AAG CAA ATA TAT AGA GAC TTA GCA ACT TTG CAA CAA ATT
116   A   A   L   N   N   G   S   T   N   K   Q   I   Y   R   D   L   A   T   L   Q   Q   I

436  GGC GAT TTC AAA AAT GCT TTA GTG TCC AGG AAA AAG TAT TGG GAA GCA TTC CTT GGT TAC CGT GCC AAC
139   G   D   F   K   N   A   L   V   S   R   K   K   Y   W   E   A   F   L   G   Y   R   A   N

505  TGG ACA TCA TTG GCT GTG GCA CAA GAT GTG GAG AGG CAA CAA GCT ATT AAC ACT TTA TCT CAG
162   W   T   S   L   A   V   A   Q   D   V   E   R   Q   Q   A   I   N   T   L   S   Q

574  TTT GAA AAA CTC GCT GAG GGA AAA ATA TCT GAT TCC GAG AAA TAT GAA CAC AGC GAG TGT TTA ATG TAC
185   F   E   K   L   A   E   G   K   I   S   D   S   E   K   Y   E   H   S   E   C   L   M   Y

643  AAA AAC GAC ATT ATG TAT AAA GCT GCC AGT GAT AAC CAA AAG TTA CAA AAT GTA TTG AAA CAT TTG
208   K   N   D   I   M   Y   K   A   A   S   D   N   Q   K   L   Q   N   V   L   K   H   L
```

FIG. 12C

```
 712  AAT GAT ATC GAG CCA TGC GTC TTT GAT AAA TTT GGT TTA TTA GAG AGA AAA GCA ACT ATT TAC ATG AAA
 231   N   D   I   E   P   C   V   F   D   K   F   G   L   L   E   R   K   A   T   I   Y   M   K

781  TTG GGT CAA TTG AAA GAC GCG TCC ATT GTT AGA ACT CTG AAG AGA ATC ATC AAG AGA GAT AAT CCA AAT TTT AAG
 254   L   G   Q   L   K   D   A   S   I   V   R   T   L   K   R   I   I   K   R   D   N   P   N   F   K

850  TAC TAC AAA TTA CTG GAA GTA TCC TTG GGA ATC CAA GGT GAC AAT AAA TTG AAG AAG GCT TTG TAT GGA
 277   Y   Y   K   L   L   E   V   S   L   G   I   Q   G   D   N   K   L   K   K   A   L   Y   G

919  AAA CTT GAA CAA TTT TAT CCA AGA TGC GAA CCA CCC AAA TTT CCA TTC CTT CAA GAC AAA
 300   K   L   E   Q   F   Y   P   R   C   E   P   P   K   F   L   Q   D   K
                            |---------9-1-1---------→|                |--2-2, 29-1-------
 988  GAA GAG CTC AGC AAA AAA TTG AGA GAA TAT GTT CCT CAA TTG CCT CAG GTT GGT CCA GCA ACT TTT
 323   E   E   L   S   K   K   L   R   E   Y   V   P   Q   L   P   Q   V   G   P   A   T   F
                                      |-------------15-1-2-----------→|     |-------

1057  TCC AAC GTG AAA CCC CTT TAC CAA AGA AGG AAG TCC AAG GTT TCA CCA CTA TTG GAG AAA ATT GTC CTT
 346   S   N   V   K   P   L   Y   Q   R   R   K   S   K   V   S   P   L   L   E   K   I   V   L
       |------15-3-1---------------------→|
1126  GAT TAT TTG TCC GGA TTA GAT CCT ACG CAG GAT CCT CAA ATT CCT TTT ATT TGG ACC AAT TAT TAC TTG TCT
 369   D   Y   L   S   G   L   D   P   T   Q   D   P   Q   I   P   F   I   W   T   N   Y   Y   L   S

1195  CAA CAT TTC CTT TTC AAG GAT TTT CCG AAA GCC CAA GAA TAT ATC CTG AAG GCA CGT ATC ATC CTG AAC CAC ACC
 392   Q   H   F   L   F   K   D   F   P   K   A   Q   E   Y   I   L   K   A   R   I   L   K   H   T

1264  CCA ACT TTA GTT GAG TTT TAC ATC CTC AAG GCA CTA ATG GAC ACA GCG
 415   P   T   L   V   E   F   Y   I   L   K   A   L   M   D   T   A
```

FIG.12D

```
C 1333  GCT GGA ATT TTG GAG GAA CTT GAT TTG CAG GAT AGA TTT ATC AAC TGT AAA ACG GTT AAG
    438   A   G   I   L   E   E   L   D   L   Q   D   R   F   I   N   C   K   T   V   K

1402  TAC TTT TTA AGG GCT AAT ATC GAC AAG GTG GAA GTC GCG CTT TTC ACC AAA AAC GAT GAT
    461   Y   F   L   R   A   N   I   D   K   V   E   V   A   L   F   T   K   N   D   D
                                              |←----15-1-1---→|

1471  TCT GTT AAT GGT ATT AAG GAC TTA CAC CTT GTG GAA GCT TCT TGG TTC ATC GTA GAA GCC
    484   S   V   N   G   I   K   D   L   H   L   V   E   A   S   W   F   I   V   E   A

1540  TAT TAT AGA CTA TAC CTG GAT AGA AAA AAG AAG AAA TTA GAC GAT CTA TCG CTT AAA GAG
    507   Y   Y   R   L   Y   L   D   R   K   K   K   K   L   D   D   L   S   L   K   E

1609  AGT GAT AAA AGC GAA CAA ATT GCG ATT CAA CAA AAT CAA TGG CTT GTT CGC AAA TAT AAA
    530   S   D   K   S   E   Q   I   A   I   Q   Q   N   Q   W   L   V   R   K   Y   K

1678  TTG GCG CTG AAA AGA TTC AAC GCT ATT CCA AAG TTT TAT AGA GCC TAT CTG GAG ATG TTA
    553   L   A   L   K   R   F   N   A   I   P   K   F   Y   R   A   Y   L   E   M   L

1747  CAT TCA TAC TGT ATG AGA AAA GGT ACG CCA AGA GCC TAT GCA TCA AAG CTT TAC TTT CAA
    576   H   S   Y   C   M   R   K   G   T   P   R   A   Y   A   S   K   L   Y   F   Q
                                                                |←----27-1---

1816  TAT ACC AAA CCC ATG TAT GTT CGC GCA ATG TAT CTG GAA GCA TCA GAT GAA AAT TCA GAT
    599   Y   T   K   P   M   Y   V   R   A   M   Y   L   E   A   S   D   E   N   S   D
              |←---9-2-2---→|                                        ---10-3-1---

1885  CGC TTA AAA AGA AAG TCC GAT TCT TTA GAT GAA GCA GCT ATG AAA AAC CGG AGA AAG AAG
    622   R   L   K   R   K   S   D   S   L   D   E   A   A   M   K   N   R   R   K   K

1954  AGC CAA AAG AAA GCT TAT CCG AGT GAT CAA GAT GTA TTC GGC GAA AAG TTG ATT GAA ACC
    645   S   Q   K   K   A   Y   P   S   D   Q   D   V   F   G   E   K   L   I   E   T
                                              |←---11-3-2---→|                |←

2023  AGT GTT GCT GCT TAT CCG AGT GAT CAA GAT CAA TTT TAT AAT AAC TAC TCC ATG CAA GTC
    668   S   V   A   A   Y   P   S   D   Q   D   Q   F   Y   N   N   Y   S   M   Q   V

2092  CCA ATG GAG GAC TTC GCT ACC GAA TTT GAA TTT GGA AAG TTA GCT CGA GAA GAC AGG GAT
    691   P   M   E   D   F   A   T   E   F   E   F   G   K   L   A   R   E   D   R   D
              ---35-2, 39-1---→|

2161  TAT ATT TTG GAC TTT GAA TTT AAC TAC AGA ATT GGA AAG TTA TGC TTT GCT TCT CTA AAC AAA
    714   Y   I   L   D   F   E   F   N   Y   R   I   G   K   L   C   F   A   S   L   N   K
```

FIG. 12E

```
C 2230 TTC GCT AAG AGA TTT GGC ACC ACG AGC GGT TTA TTT GGT AGT ATG GCC ATT GTT TTG TTA CAT GCC ACA
  737   F   A   K   R   F   G   T   T   S   G   L   F   G   S   M   A   I   V   L   L   H   A   T

2299 AGA AAC GAC ACC CCC TTT GAT CCA ATT TTG AAG AAA GTA GTC ACG AAG AGC CTT GAA AAA GAG TAT TCT
   760  R   N   D   T   P   F   D   P   I   L   K   K   V   V   T   K   S   L   E   K   E   Y   S

2368 GAA AAT TTC CCA TTA AAC GAA ATA TCT AAC AGC TTC GAT TGG CTG AAT TTC TAC CAA GAA AAA TTC
   783  E   N   F   P   L   N   E   I   S   N   S   F   D   W   L   N   F   Y   Q   E   K   F

2437 GGT AAG AAT GAT ATA AAT GGC CTG CTA TTT CTT TCT CCC TTG GAG CCT CAC TCC CAG AAC GAA ATT CTA CAG
   806  G   K   N   D   I   N   G   L   L   F   L   Y   R   Y   D   D   V   P   I   G   S   S

2506 AAT TTC AAA GAA ATG ATT ATT AGC AGT CTT TCT CCC TTG GAG CCT CAC TCC CAG AAC GAA ATT CTA CAG
   829  N   L   K   E   M   I   I   S   S   L   S   P   L   E   P   H   S   Q   N   E   I   L   Q

2575 TAT TAC TTG TAG CCTGCAACTCCTCAATGTGTCAATTAACTCTTACTTAATTTATGTATATATTTTTTATGTATATGCTTATATGCA
   852  Y   Y   L   *

2662 TGGCGCATATGCTCATAAAGATACATTGTTATAGGTCAAAAAAAAAAAAAAAAAA.....3'
```

ISOLATION, PURIFICATION, CHARACTERIZATION, CLONING AND SEQUENCING OF N$^\alpha$-ACETYLTRANSFERASE

CROSS-REFERENCE TO RELATED APPLICATIONS

This application is a division of application Ser. No. 07/533,353, filed Jun. 5, 1990, now U.S. Pat. No. 5,128,459 which is a division of 07/284,344, filed Dec. 14, 1988, now U.S. Pat. No. 4,966,848 which is a continuation-in-part application of U.S. patent application Ser. No. 153,361, filed Feb. 8, 1988, now abandoned, the contents of which are fully incorporated herein by reference.

FIELD OF THE INVENTION

The invention is directed to the isolation, purification, characterization, cloning and sequencing of N$^\alpha$-acetyltransferase and to the enzyme itself.

BACKGROUND OF THE INVENTION

An acetyl moiety was discovered as the amino-terminal blocking group of viral coat protein in 1958 (Narita, K., Biochim Biophys. Acta 28:184-191 (1958) and of hormonal peptide in 1959 (Harris J. I., Biochem. J. 71:451-459 (1959). Since then, a large number of proteins in various organisms have been shown to possess acetylated amino-terminal residues. For example, mouse L-cells and Ehrlich ascites cells have about 80% of their intracellular soluble proteins N$^\alpha$-acetylated (Brown, J. I. and Roberts, W. K., J. Biol. Chem. 251:1009 (1976) and Brown, J. L. J. Biol. Chem. 254:1447 (1979)). In lower eukaryotic organisms, about 50% of the soluble proteins are acetylated (Brown, J. L., Int'l Congr. Biochem. Abstr. (Internation Union of Biochemistry, Canada) Vol. 11:90 (1979)). These data demonstrate that N$^\alpha$-acetyl is a very important blocking group. It has been suggested that the biological function of this blocking group may be to protect against premature protein catabolism (Jornvall, H., J. Theor. Biol 55:1-12 (1975)) and protein proteolytic degradation (Rubenstein, P. and Deuchler, J., J. Biol. Chem. 254:11142 (1979)). However, in mouse L-cells such N$^\alpha$-acetylation does not apparently have this biological function (Brown, J. L., J. Biol. Chem. 254:1447 (1979)).

Although a clear general function for N-acetylation has not been assessed with certainty, some specific effects for a small number of proteins have been observed. Nonacetylated NADP-specific glutamate dehydrogenase in a mutant of Neuro spora crassa is heat-unstable, in contrast to the acetylated form (Siddig et al., J. Mol. Biol. 137:125 (1980)). A mutant of Escherichia coli, in which ribosomal protein S5 is not acetylated, exhibits thermosensitivity (Cumberlidge, A. G. and Isono, K., J. Mol. Biol. 131:169 (1979)). N$^\alpha$-acetylation of two of the products from the precursor protein proopiomelanocortin has a profound regulatory effect on the biological activity of these polypeptides; the opioid activity of $\beta$-endorphin is completely suppressed, while the melanotropic effect of $\alpha$-MSH is increased if N$^\alpha$-acetylated (Smyth et al., Nature 279:252 (1970); Smyth, D. G. and Zakarian, S., Nature 288:613 (1980); and Ramachandran, J. and Li, C. H., Adv. Enzymol. 29:391 (1967)). Both acetylated and nonacetylated cytoplasmic actin from cultured Drosophila cells participate in the assembly of microfilaments, the latter, however, with less efficiency (Berger et al., Biochem. Genet. 19:321 (1981)).

More recently, the rate of protein turnover mediated by the ubiquitin-dependent degradation system was shown to depend on the presence of a free $\alpha$-NH2 group at the N-terminus of a protein (Hershko et al., Proc. Nat'l Acad. Sci. U.S.A. 81:9021-9025 (1984) and Bachmair et al., Science 234:179-186 (1986)), suggesting that N$^\alpha$-acetylation may have a role in impeding protein turnover.

Given the importance of N-acetylation for the function and the ability of these N-acetylated proteins to modulate cellular metabolism, it is of interest to examine the subcellular location, substrate specificity, and regulation of protein acetyltransferase. In order to cast light on the biological implications of the acetylation and to elucidate the enzymatic mechanism of the reaction, as a first step, an enzyme must be isolated that is able to catalyze the aminoterminal acetylation in order to investigate its substrate specificity. The existence of such an acetyltransferase has been demonstrated and studied in E. coli for ribosomal protein L12 (Brot et al., Arch. Biochem. Biophys. 155:475 (1973)), in rat liver (Pestana, A. and Pitot, H. C. Biochemistry 14:1404 (1975); Green et al., Can. J. Biochem. 56:1075 (1978)); and Pestana, A. and Pitot, H. C. Biochemistry 14:1397 (1975)), calf lens (Granger et al., Proc. Nat'l Acad. Sci. U.S.A. 73:3031 (1976)), rat pituitary (Woodford, T. A. and Dixon J. E., J. Biol. Chem. 254:4993 (1979); Pease, K. A. and Dixon J. E., Arch. Biochem. Biophys. 212:177 (1981); and Glembotski, C. C., J. Biol. Chem. 257:10501 (1982)), ox pituitary (Massey D. E. and Smyth, D. G., Biochem. Soc'y Trans. 8:751-753 (1980), hen oviduct (Tsunasawa et al., J. Biochem. 87:645 (1980)), and in wheat germ (Kido et al., Arch. Biochem. Biophys. 208:95 (1981)). However, isolation of this enzyme was not achieved, and only the enzyme from hen oviduct has been partially purified about 40-fold (Tsunasawa et al., J. Biochem. 87:645 (1980). The inability to isolate and purify these enzymes is due to their low concentration and extreme instability after purification.

SUMMARY OF THE INVENTION

According to this invention, an N$^\alpha$-acetyltransferase which transfers an acetyl group from acetyl coenzyme A to the N-terminal amino group of polypeptides was isolated and purified 4600-fold to homogeneity. The invention therefore relates to the purification to homogeneity of N$^\alpha$-acetyltransferase and to the purified N$^\alpha$-acetyltransferase.

The N$^\alpha$-acetyltransferase was purified by successive purification steps using ion exchange, hydroxylapatite, and affinity chromatography. The N$^\alpha$-acetyltransferase is composed of two identical subunits. The molecular weight ($M_r$) of the native enzyme was estimated to be 180,000±10,000 daltons by gel filtration chromatography, and the $M_r$ of each subunit was estimated to be 95,000±2,000 daltons by SDS-PAGE. The enzyme has a pH optimum near 9.0 and displays a maximum activity at temperatures from 30° to 42° C. By chromatofocusing on Mono-P, the isoelectric point of this enzyme was determined to be 4.3. Among a series of divalent cations, $Cu^{2+}$ and $Zn^{2+}$ were demonstrated to be the most potent inhibitors of the enzyme. By using several synthetic peptides, it has been demonstrated that the enzyme has a defined substrate specificity dependent on the amino-terminal residue and that the enzyme may be involved in N-terminal processing of yeast proteins.

Further, the complete amino acid sequence for the yeast N$^\alpha$-acetyltransferase was deduced from cDNA. The N$^\alpha$-acetyltransferase enzyme was cloned from a yeast λgt11 cDNA library and a full-length cDNA encoding yeast N$^\alpha$-acetyltransferase was sequenced. Southern blot hybridizations of genomic and chromosomal DNA reveal that the enzyme is encoded by a single gene which is localized on chromosome IV. This gene is designated herein as "AAA1" (Amino-terminal Alpha-amino Acetyltransferase 1). This yeast cDNA forms the basis for elucidating the biological function and regulation of N$^\alpha$-acetyltransferase in eukaryotic protein synthesis and degradation. Further, by using site-directed mutagenesis, the catalytic mechanism and regulation of N$^\alpha$-acetyltransferase may be elucidated.

DETAILED DESCRIPTION OF THE INVENTION

N$^\alpha$-acetyltransferase is an enzyme which transfers an acetyl group from acetyl coenzyme A to the amino-terminal of a protein or polypeptide. The structure of acetyl coenzyme A is given below:

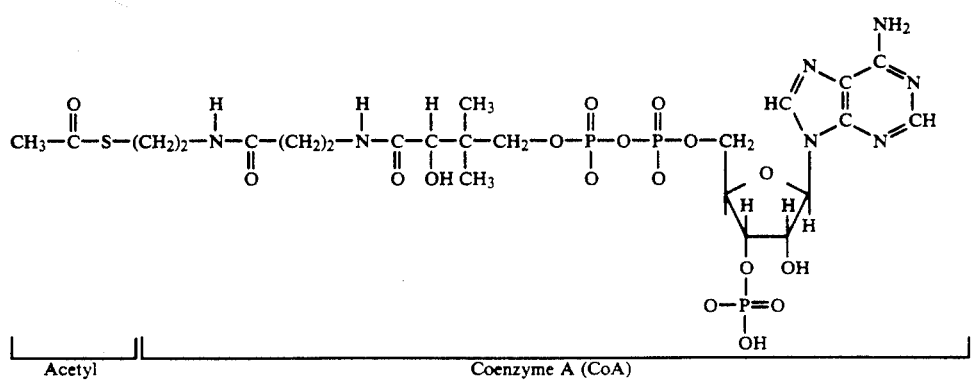

I. Isolation, Purification, and Sequencing of N$^\alpha$-acetyltransferase

In accordance with this invention, N$^\alpha$-acetyltransferase can be isolated from a sample containing the enzyme. Any sample that contains the enzyme may be used as a starting material according to the methods described in this invention. N$^\alpha$-acetyltransferase appears to be ubiquitous, being found in all eukaryotes, including plants, animals, and multicellular organisms. The enzyme is also believed to be present in prokaryotes. Therefore, any source of N$^\alpha$-acetyltransferase is contemplated in this invention. As used herein, the sample containing the enzyme will be referred to simply as "sample," which is intended to include N$^\alpha$-acetyltransferase containing sample.

The isolation and purification of N$^\alpha$-acetyltransferase will hereinafter be described from a yeast sample, although it is to be understood that other samples could be used as the source material. The preferred method for purifying the N$^\alpha$-acetyltransferase of the present invention is that of Lee, F.-J. S., et al. (*J. Biol. Chem.* 263:14948-14955 (1988), which reference is incorporated by reference herein in its entirety).

Yeast cells were spheroplasted by lyticase and homogenized in hypotonic buffer with a Dounce homogenizer. Yeast acetyltransferase was released from cells lysate into buffer B containing 0.2M KCl by gently shaking. After centrifugation, the supernatant was concentrated by ultrafiltration with PM-30 membrane and dialyzed overnight against HDG buffer (20 mM HEPES-K$^+$, pH 7.4, 0.5 mM DTT, 10% (v/v) glycerol and 0.02% NaN$_3$) containing 0.2M KCl. The yeast acetyltransferase is not a stable enzyme and 10% of glycerol was used to extend the half-life of the enzyme.

Figure 1:
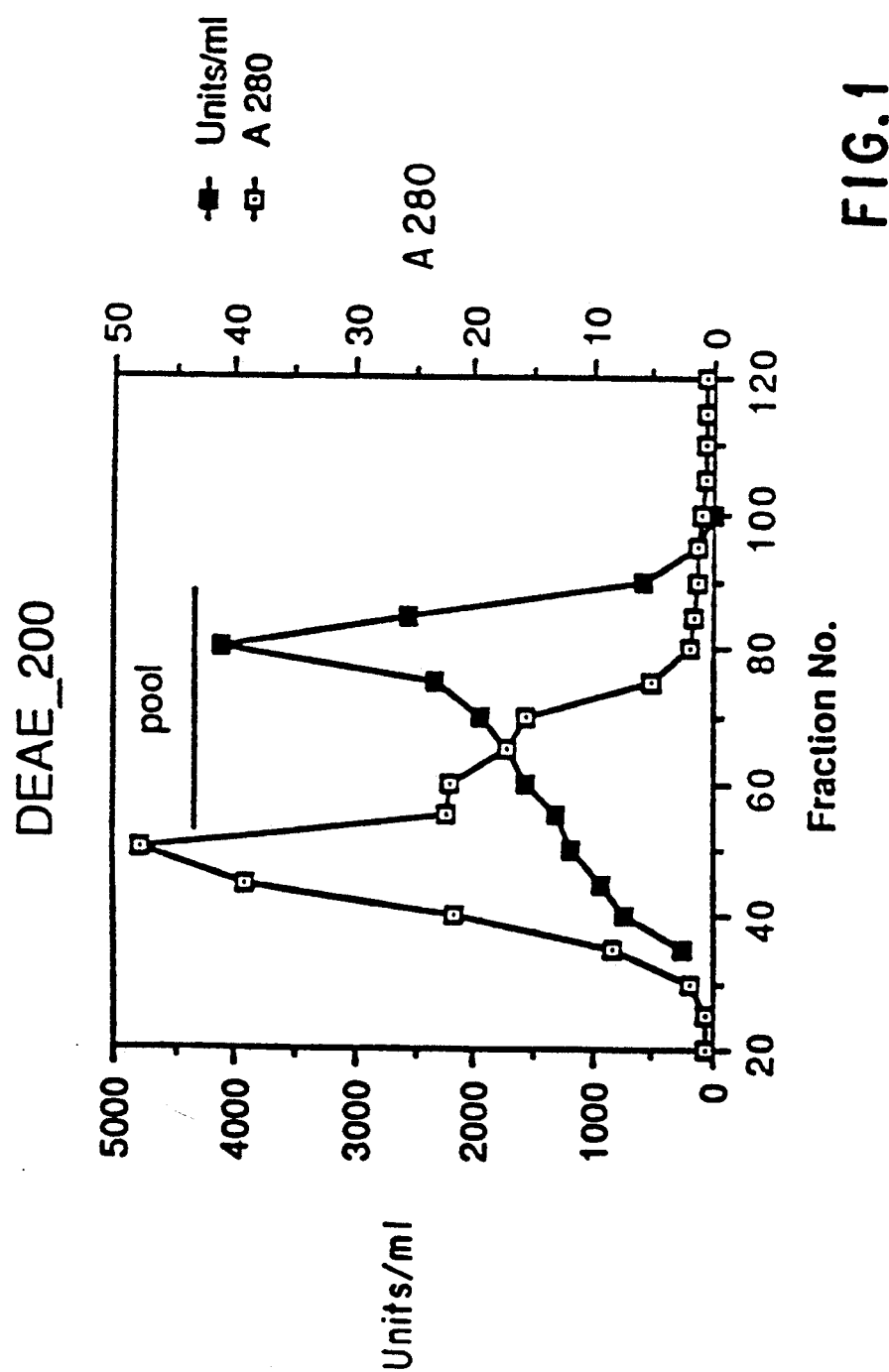
FIG. 1 shows the chromatography of the yeast acetyltransferase on DEAE-Sepharose (0.2M KCl). An aliquot of the supernatant from yeast homogenates was chromatographed on DEAE-Sepharose (0.2M KCl). The eluant for $A_{280}$ was measured and acetyltransferase activity was assayed as described in the Examples. Fractions containing acetyltransferase activity were pooled as indicated by the horizontal bar.

The next step in the purification was removal of residual cell biomaterials in the supernatant to avoid protein-biomaterials aggregation in subsequent steps. Ion exchange can be used for this procedure. In this step, the ion exchange used was DEAE-Sepharose chromatography with constant salt (0.2M KCl) elute which was found to be most gentle procedure. About 80% of biomaterials or proteins was removed with a 107% recovery of yeast acetyltransferase activity. FIG. 1 shows the chromatography of the yeast acetyltransferase on DEAE-Sepharose (0.2M KCl).

Figure 2:
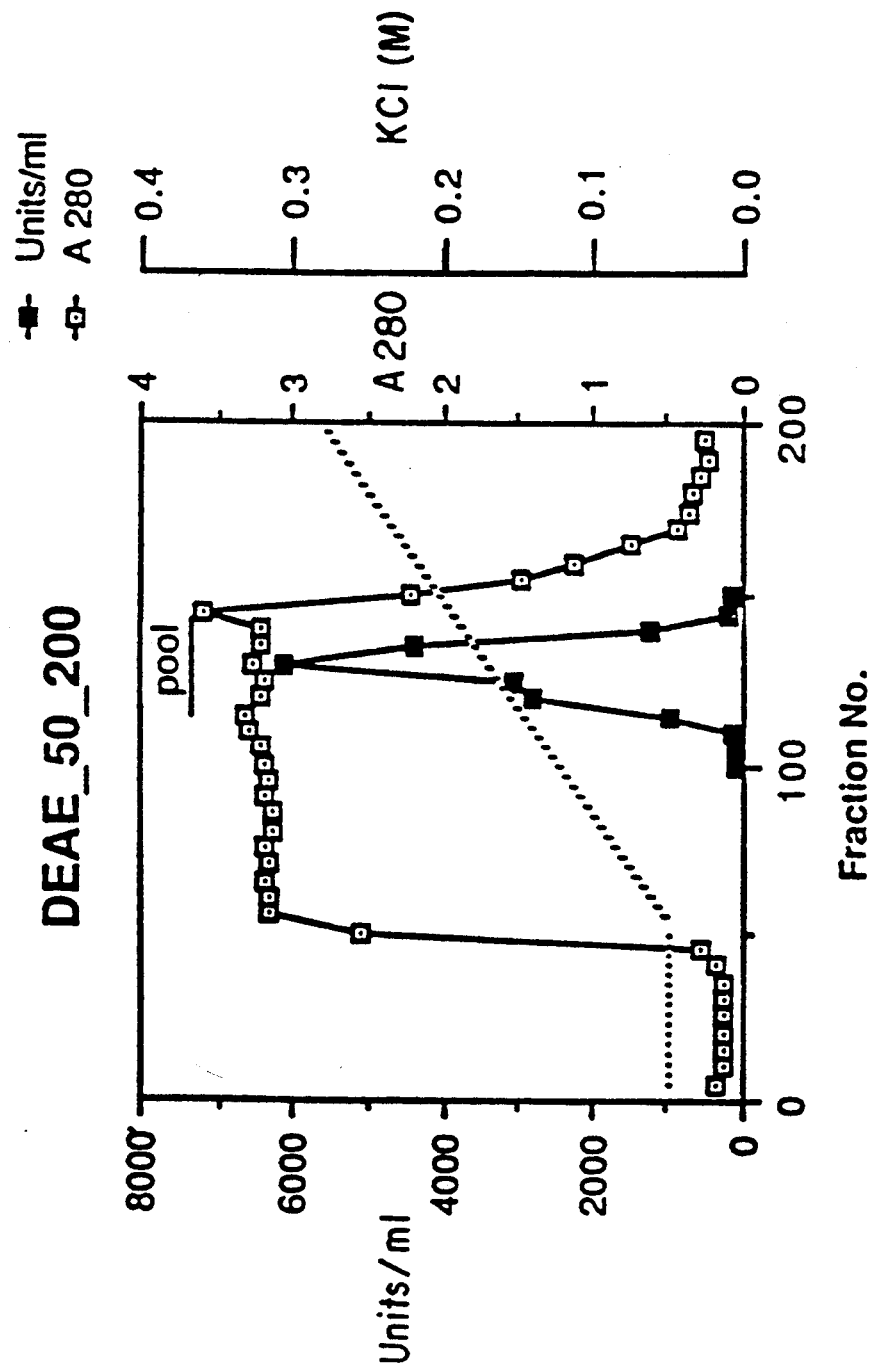
FIG. 2 shows the chromatography of the yeast acetyltransferase on DEAE Sepharose (0.05 to 0.5M KCl). The acetyltransferase pool from DEAE-Sepharose (0.2M KCl) was concentrated, dialyzed, and an aliquot was chromatographed on a DEAE-Sepharose (0.05 to 0.5M KCl) and analyzed for $A_{280}$, conductivity, and acetyltransferase activity as described in the Examples. Fractions containing acetyltransferase activity were pooled as indicated by the horizontal bar.

Peak fractions from DEAE-Sepharose (0.2M KCl) column were pooled, concentrated, dialyzed against HDG buffer containing 0.05M KCl, and loaded onto a DEAE-Sepharose column with a continuous salt gradient (0.05 to 0.5M KCl) elute. FIG. 2 shows the chromatography of the yeast acetyltransferase on DEAE-Sepharose (0.05 to 0.5M KCl). A single symmetrical activity peak was generated which centered at 0.18M KCl. In this step, a 204% recovery of the acetyltransferase activity was achieved (Table 1), suggesting that an inhibitor was removed.

Figure 3:
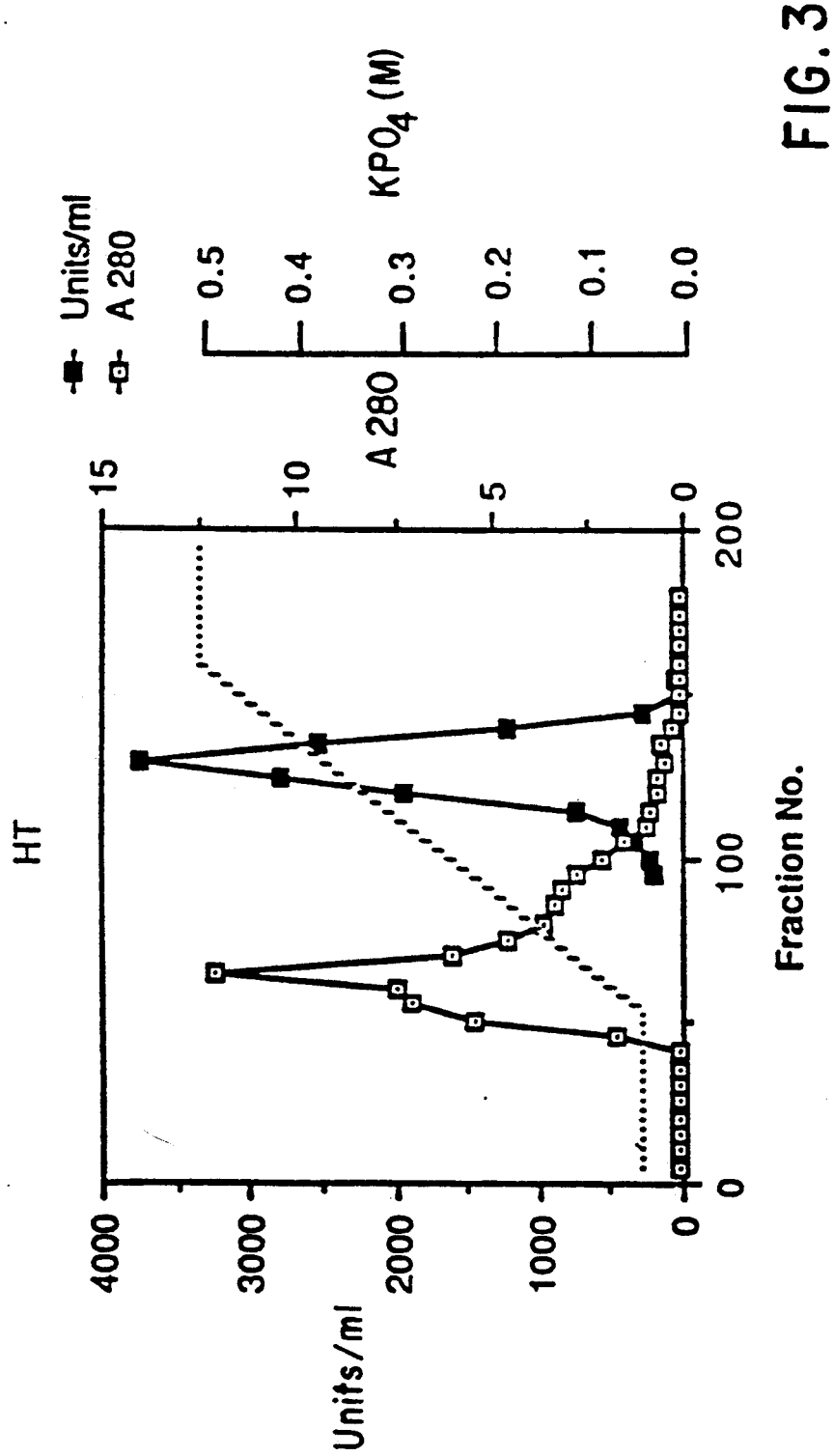
FIG. 3 shows the chromatography of the yeast acetyltransferase on hydroxylapatite. The acetyltransferase pool from DEAE-Sepharose (0.05 to 0.5M KCl) was concentrated, dialyzed, and an aliquot was chromatographed on a hydroxylapatite column and analyzed for $A_{280}$, conductivity, and acetyltransferase activity as described in the Examples. Fractions containing acetyltransferase activity were pooled as indicated by the horizontal bar.

Peak fractions from DEAE-Sepharose (0.05 to 0.5M KCl) were pooled, concentrated, dialyzed into 0.05M potassium phosphate buffer, pH 7.4, p.5 mM DTT, 10% (v/v) glycerol, 0.02% NaN$_3$ and applied to an adsorption column using hydroxylapatite. As is known in the art, a hydroxylapatite column will selectively adsorb proteins onto calcium ions in the calcium hydroxyphosphate packing. The hydroxylapatite column was eluted with a linear salt gradient and a single peak of activity at 0.36M potassium phosphate was generated. In this step the major peak of total protein elution occurred at 0.5 to 2.0M potassium phosphate. FIG. 3 shows the chromatography of the yeast acetyltransferase on hydroxylapatite. The acetyltransferase pool from DEAE-Sepharose (0.05 to 0.5M KCl) was concentrated, dialyzed, and an aliquot was chromatographed on a hydroxylapatite column and analyzed for A$_{280}$, conductivity, and acetyltransferase activity as described in the Examples. Fractions containing acetyltransferase activity were pooled as indicated by horizontal bar.

Figure 4:
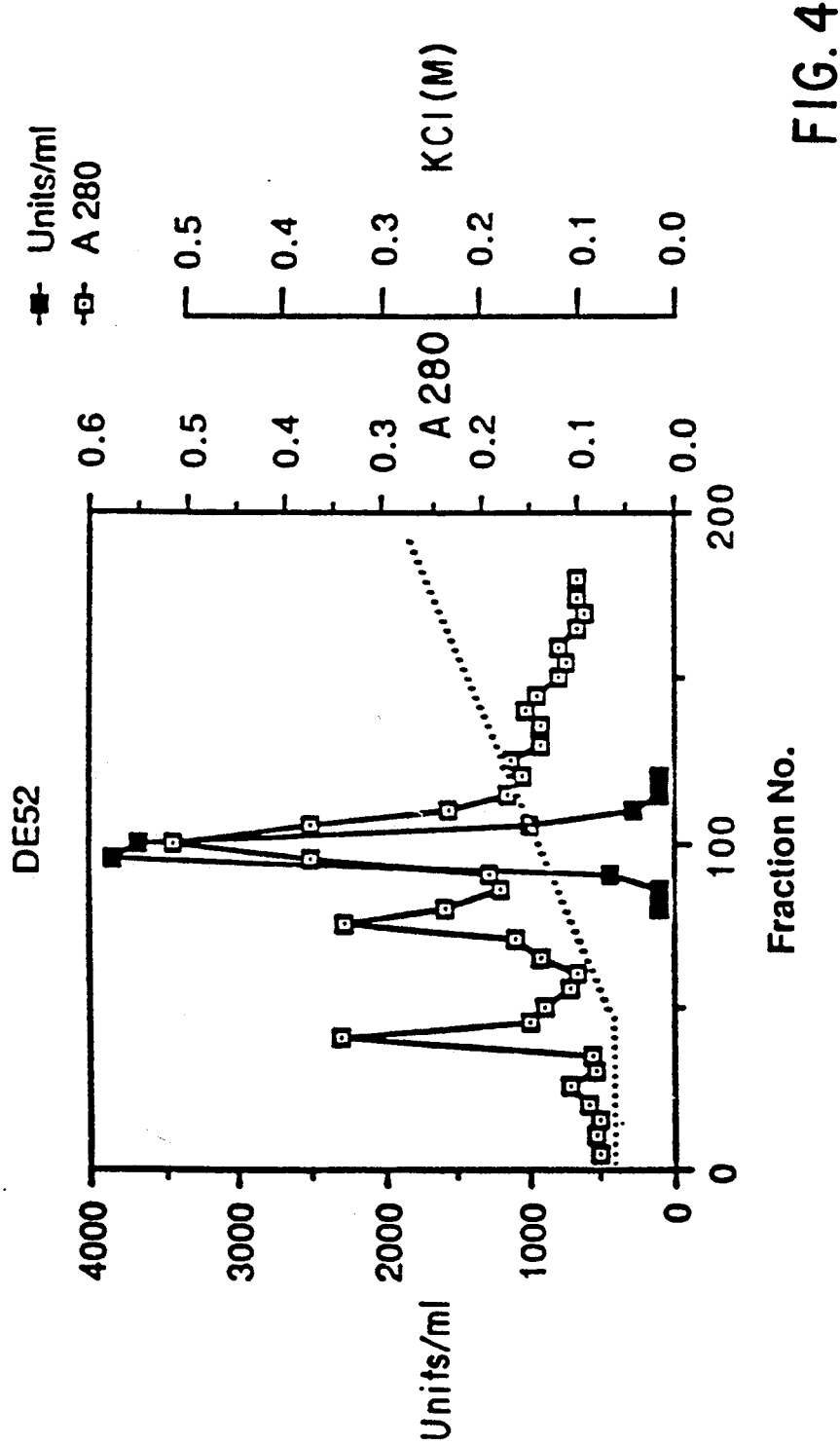
FIG. 4 shows the chromatography of the yeast acetyltransferase on DE52 cellulose. The acetyltransferase pool from hydroxylapatite was concentrated, dialyzed, and an aliquot was chromatographed on a DE52 cellulose column and analyzed for $A_{280}$, conductivity, and acetyltransferase activity as described in the Examples. Fractions containing acetyltransferase activity were pooled as indicated by the horizontal bar.

Peak fractions from hydroxylapatite column were pooled, concentrated, dialyzed against HDG buffer containing 0.05M KCl, and loaded onto an ion exchange column, DE52-cellulose, with a continuous salt gradient. A single activity peak was generated which centered at 0.14M KCl. FIG. 4 shows the chromatography of the yeast acetyltransferase on DE52 cellulose.

Figure 5:
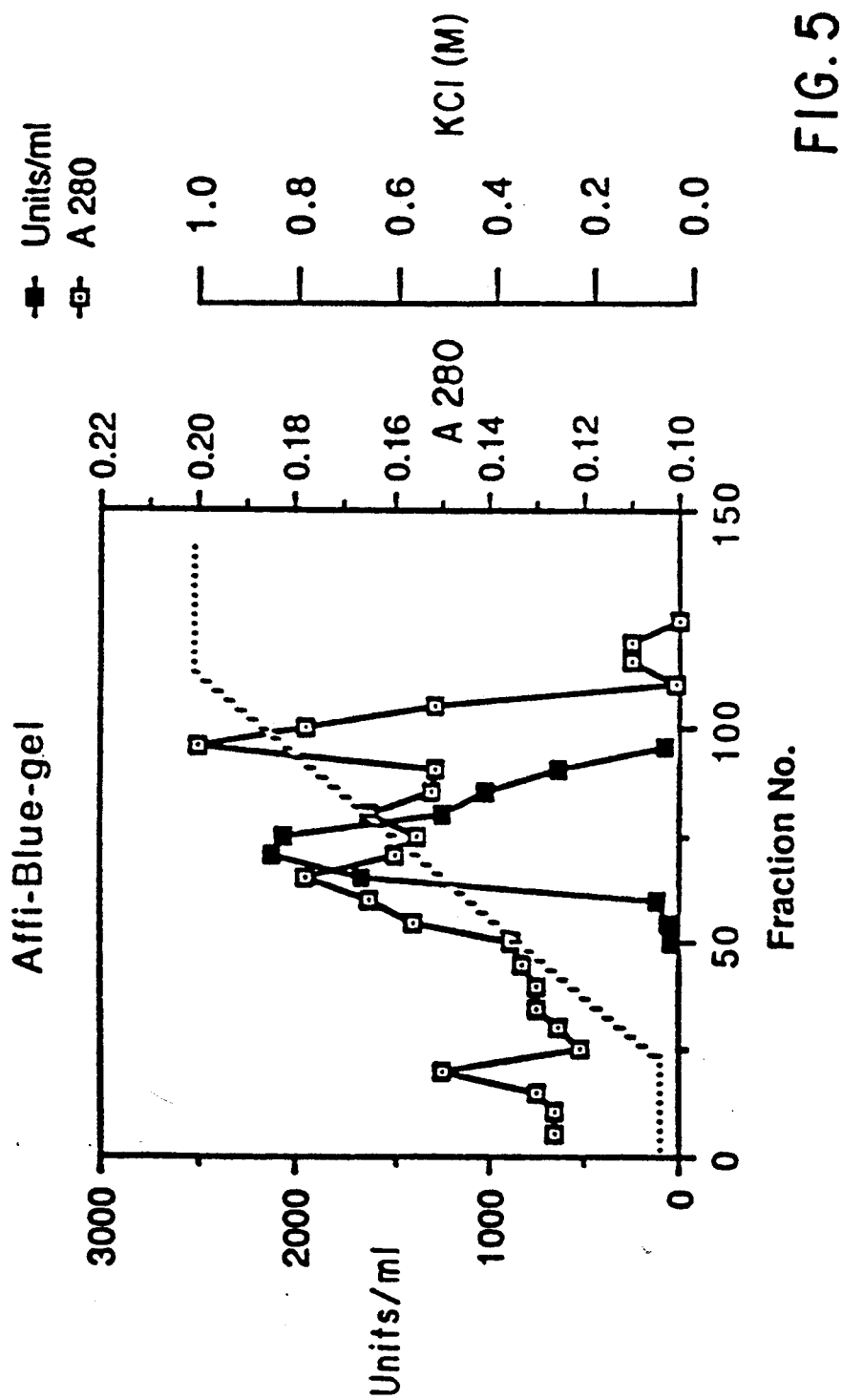
FIG. 5 shows the chromatography of the yeast acetyltransferase on Affi-Blue gel.

Peak fractions from DE52-cellulose column were pooled, concentrated, dialyzed against HDG buffer containing 0.05M KCl, and loaded onto an affinity column, Affi-Blue gel, with a continuous salt gradient (0.05 to 1.0M KCl) elute. A single activity peak was generated which centered at 0.6M KCl. FIG. 5 shows the chromatography of the yeast acetyltransferase on Affi-Blue gel column and analyzed for A$_{280}$, conductivity, and acetyltransferase activity as described above in "Materials and Methods." Fractions containing acetyltransferase activity were pooled as indicated by horizontal bar.

Using this series of chromatography steps, yeast acetyltransferase was purified approximately 4600-fold over the cell extract with a 27% yield as seen in Table 1.

TABLE 1
PURIFICATION OF N-ACETYLTRANSFERASE FROM YEAST

| Step | Activity (Units) | Protein (mg) | Specific Activity (Unit/mg) | Purification (fold) | Yield (%) |
|---|---|---|---|---|---|
| 1. Crude Extract | 30200 | 17700 | 1.7 | 1.0 | 100 |
| 2. DEAE-Sepharose[a] | 32200 | 3710 | 8.7 | 5.1 | 107[b] |
| 3. DEAE-Sepharose[c] | 61500 | 1470 | 41.8 | 24.5 | 204[b] |
| 4. Hydroxlapatite | 19300 | 53.6 | 360 | 210 | 64 |
| 5. DEAE-Cellulose | 12700 | 8.58 | 1500 | 870 | 42 |
| 6. Affi-Blue Gel | 8160 | 1.05 | 7800 | 4600 | 27 |

[a]The results for step 2 are the combined yields of two chromatographies. Elution was 0.2 M KCl.
[b]An inhibitor was removed by this step
[c]Elution was 0.05 to 0.2 M KCl As used herein, the term "substantially pure" or "substantially purified" is meant to describe N$^\alpha$-acetyltransferase which is substantially free of any compound normally associated with the enzyme in its natural state, i.e., free of protein and carbohydrate components. The term is further meant to describe N$^\alpha$-acetyltransferase which is homogeneous by one or more purity or homogeneity characteristics used by those of skill in the art. For example, a substantially pure N$^\alpha$-acetyltransferase will show constant and reproducible characteristics within standard experimental deviations for parameters such as the following: molecular weight, chromatographic techniques, and such other parameters. The term, however, is not meant to exclude artificial or synthetic mixtures of the enzymes with other compounds. The term is also not meant to exclude the presence of minor impurities which do not interfere with the biological activity of the enzyme, and which may be present, for example, due to incomplete purification.

II. Identification, Purification, and Characterization of $N^\alpha$-acetyltransferase

Molecular Weight

Figure 6:
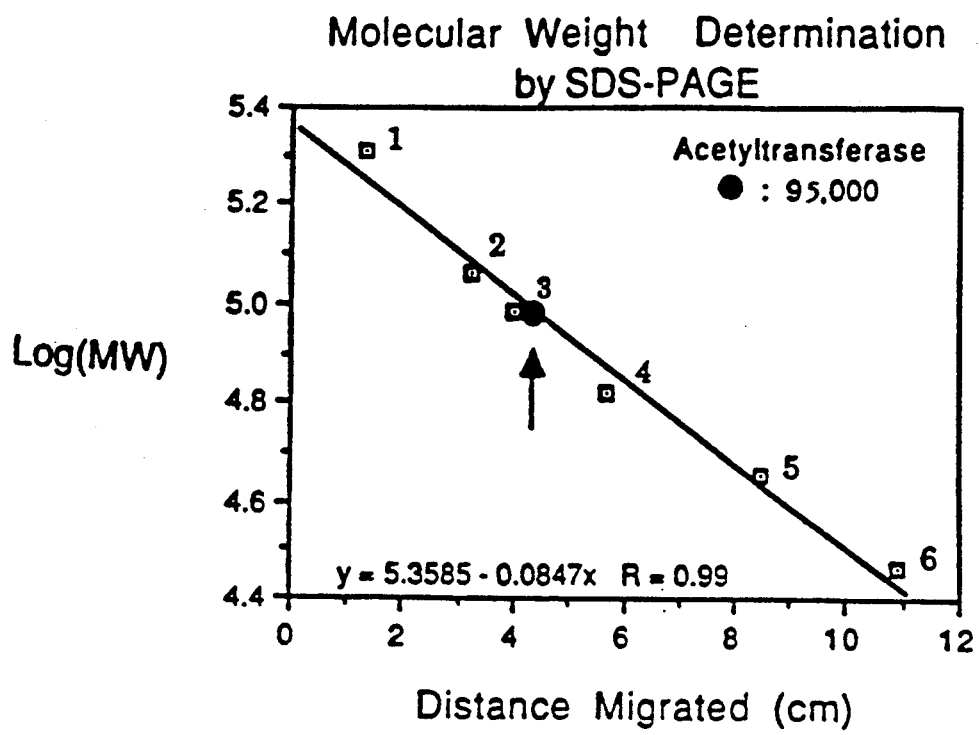
FIG. 6 shows the estimation of the molecular weight of denatured yeast acetyltransferase by SDS-PAGE.
Figure 7:
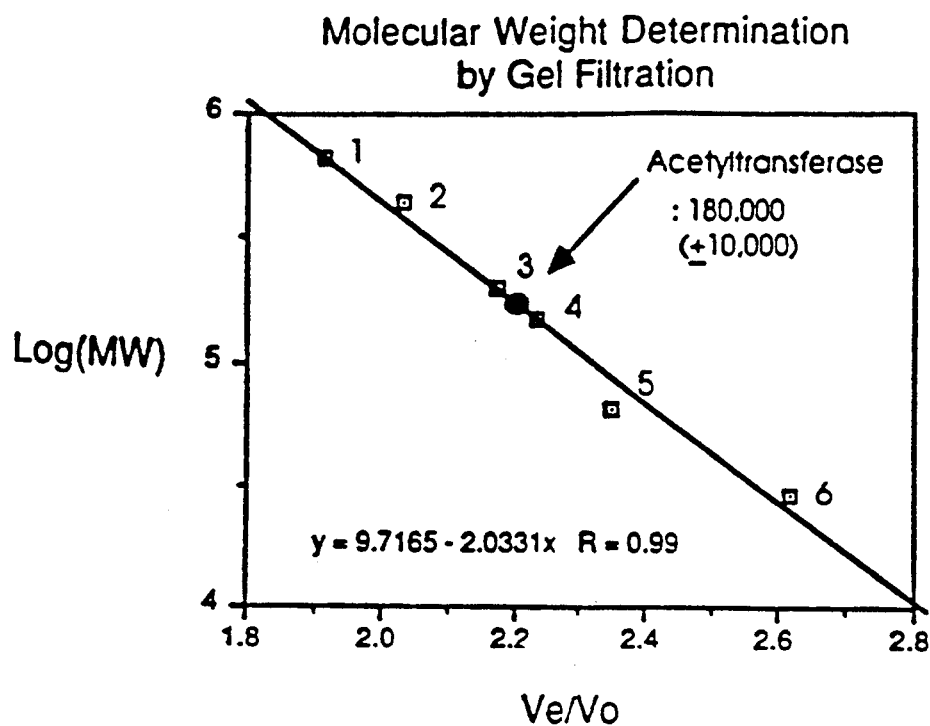
FIG. 7 shows the estimation of the molecular weight of native yeast acetyltransferase by gel filtration. The purified enzyme was applied to a Sepharose CL-4B column (2.5×96 cm). The apparent molecular weight of native yeast acetyltransferase was calculated from the relative elution volume of standard proteins to be 180,000±10,000 daltons. The elution volume was determined by absorbance at 280 nm and enzyme activity.

SDS-polyacrylamide gels of the purified sample reveal a single band when stained with Coomassie blue. The electrophoresis was performed according to the method of Laemmli, U.K., Nature 227:680-685 (1970) using a 8% gel. The gel was stained with Coomassie blue. Standard proteins of 45, 66, 97, 116, and 205 molecular weight were run with the crude extract, DEAE-Sepharose pool, DEAE-Sepharose pool, hydroxylapatite pool, DEAE-cellulose pool and Affi-Blue-gel pool. SDS-polyacrylamide gel electrophoresis showed that the purified enzyme has a molecular weight of 95,000±2,000 daltons. FIG. 6 shows the estimation of the molecular weight of denatured yeast acetyltransferase by SDS-PAGE. The molecular weight of denatured yeast acetyltransferase was calculated by using standard proteins. Gel filtration chromatography on Sepharose CL-4B showed that the native molecular weight of the acetyltransferase is approximately 180,000 daltons. FIG. 7 shows the estimation of the molecular weight of native yeast acetyltransferase by gel filtration. These data suggest that the yeast acetyltransferase is composed of two identical subunits. Purified yeast acetyltransferase was subjected to amino acid analysis. The results of this analysis are shown in Table 2.

TABLE 2

| AMINO ACID COMPOSITION OF N-ACETYLTRANSFERASE FROM YEAST[a] | |
|---|---|
| Amino Acid | Calculated Residues[b] |
| Asx | 103 |
| Thr | 24 |
| Ser | 43 |
| Glx | 96 |
| Pro | 32 |
| Gly | 39 |
| Ala | 61 |
| Val | 41 |
| Met | 3 |
| Ile | 41 |
| Leu | 106 |
| Tyr | 32 |
| Phe | 45 |
| Lys | 73 |
| His | 12 |
| Arg | 37 |

[a]Purified acetyltransferase was obtained from gel elution after SDS-PAGE.
[b]Residues per subunit of enzyme were calculated on the basis of a molecular weight of 95,000. No correction was made for the amounts of the amino acids ser and thr that are destroyed dirung the hydrolysis. Cys and trp were not determined by this method.

Biochemical Properties of $N^\alpha$-acetyltransferase

Figure 8:
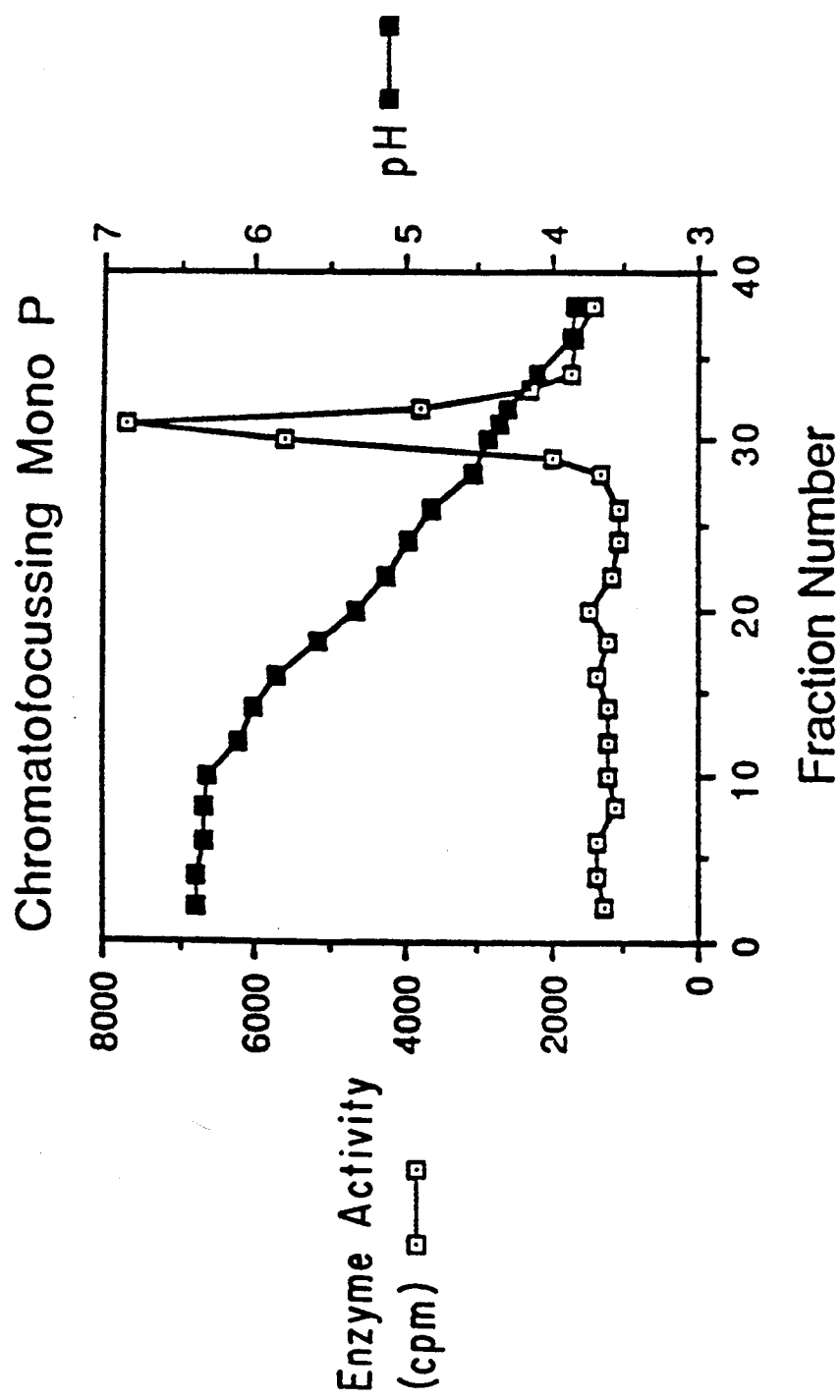
FIG. 8 shows chromatofocusing of yeast acetyltransferase on a Mono P column.

Chromatofocusing Mono P was used to determine the pI of acetyltransferase. One activity peak was observed at pH 4.3. FIG. 8 shows the chromatofocusing of yeast acetyltransferase on a Mono P column. The partial purified enzyme from DE52 column was applied to Mono P column equilibrated with 25 mM Tris-Bis buffer (pH 6) and eluted by Polybuffer 74 (pH 3.6) at the flow rate of 1 ml/min at 4° C. Elution was monitored by the absorbance at 280 nm, and 0.5 ml fraction were collected for measurement of pH and enzyme activity.

Figure 9:
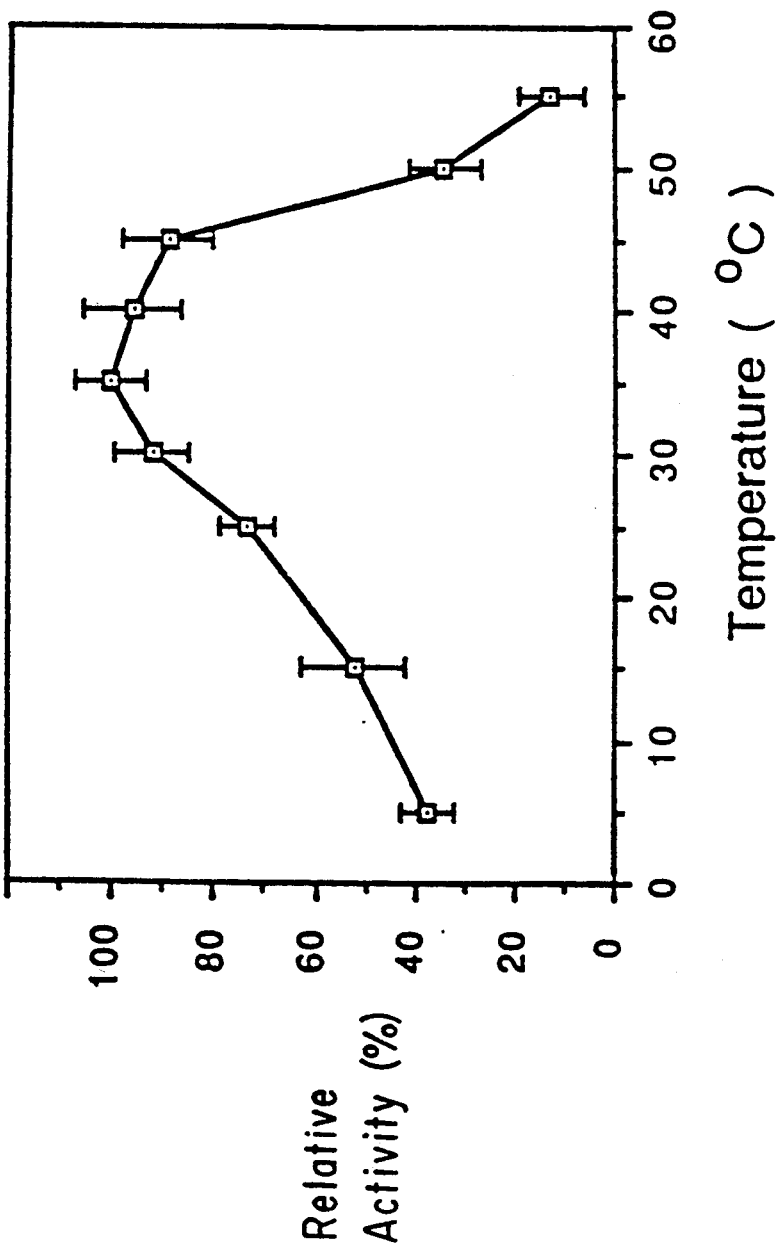
FIG. 9 shows the effect of temperature on yeast acetyltransferase.
Figure 10:
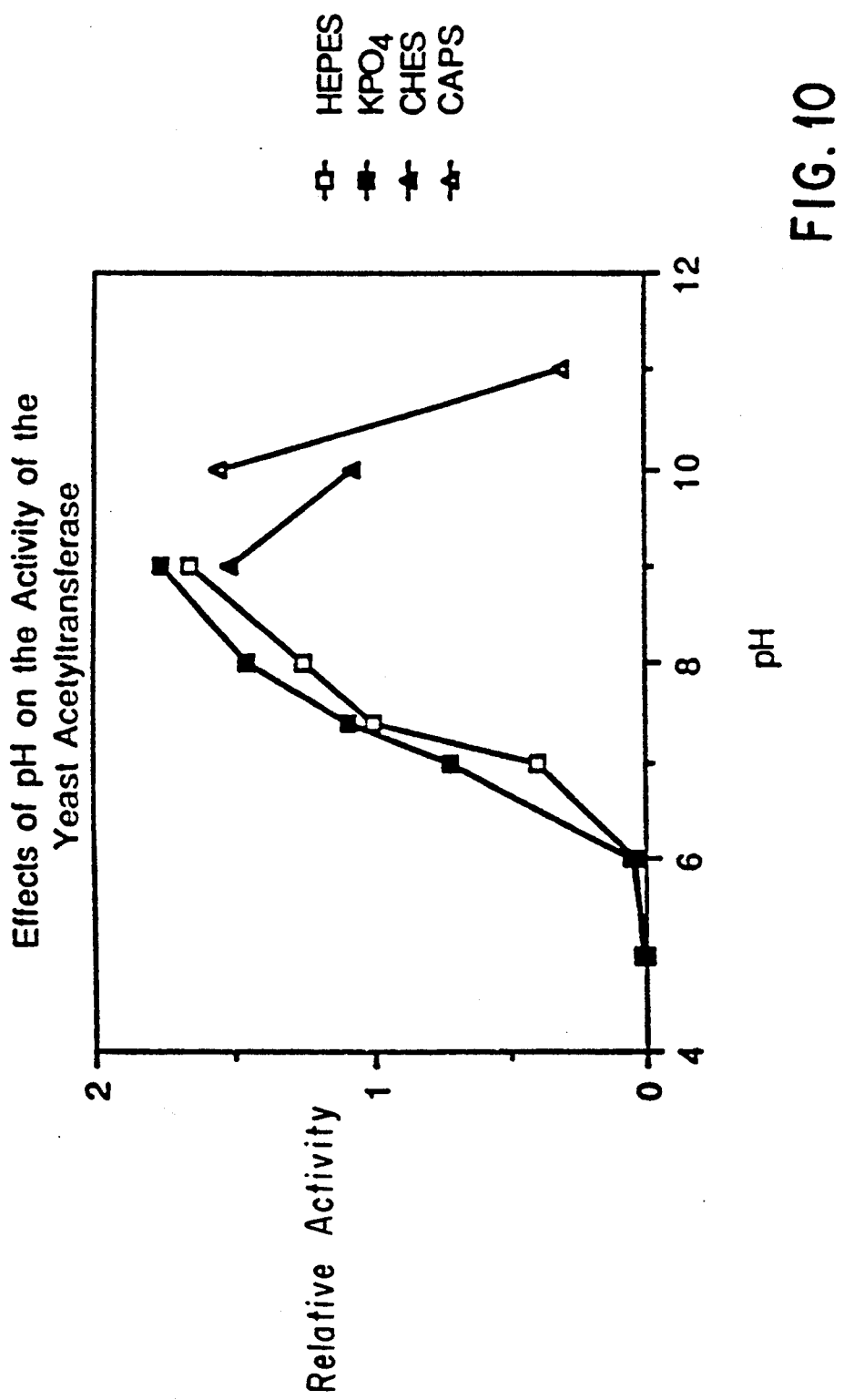
FIG. 10 shows the specific activity of yeast acetyltransferase determined in 50 mM HEPES, potassium phosphate, CHES, and CAPS buffers of different pH.

FIG. 9 shows the effect of temperature on yeast acetyltransferase. FIG. 10 shows the specific activity of yeast acetyltransferase was determined in 50 mM HEPES, potassium phosphate, CHES, and CAPS buffers of different pH's. The temperature optimum for yeast acetyltransferase was determined by assaying under standard conditions. Assays were performed from 5° to 55° C. as indicated in FIG. 9. The yeast acetyltransferase displays a maximum activity at temperatures from 30° to 42° C. Irreversible denaturation occurred after 1 minute at 65° C. The pH dependence of yeast acetyltransferase was measured by assaying at pH values from 5 to 11 in the presence of 50 mM HEPES, potassium phosphate, CHES, and CAPS buffers as indicated in FIG. 10. Maximum enzyme activity occurred at pH 9.0. Enzyme activity was less than 25% below pH 6.5 and above pH 11. Addition of KCl or NaCl up to 0.45M concentration did not affect the enzyme reaction. A 50% reduction in enzyme activity was observed when the assay was performed at 0.6M KCl or 0.6M NaCl.

Effect of Divalent Cations on Enzyme Reaction

The effect of various divalent cations on the enzyme activity was determined as shown in Table 3. At 1 mM concentration, $Ca^{2+}$, $Mg^{2+}$ had no effect, whereas nearly complete inhibition occurred in the presence at $Mn^{2+}$, $Fe^{2+}$, $Co^{2+}$, $Cu^{2+}$, $Zn^{2+}$, $Cd^{2+}$. $Cu^{2+}$ and $Zn^{2+}$ were the most potent inhibitors. It was verified that the observed effects of metal ions were not due to the $SO_4^{-2}$ anion.

TABLE 3

| EFFECT OF DIVALENT CATIONS ON ENZYME ACTIVITY[a] | | | |
|---|---|---|---|
| | Activity (%) Concentration (mM) | | |
| Addition | 1 | 0.1 | 0.01 |
| None | 100 | — | — |
| $CaCl_2$ | 100 | — | — |
| $MgCl_2$ | 99 | 120 | — |
| $MgSO_4$ | 120 | 120 | — |
| $MnCl_2$ | 28 | 43 | 84 |
| $CoCl_2$ | 20 | 60 | 86 |
| $CdCl_2$ | 12 | 42 | 90 |
| $FeSO_4$ | 12 | 53 | 78 |
| $CuSO_4$ | 0 | 0 | 58 |
| $ZnSO_4$ | 0 | 0 | 40 |

[a]Yeast acetyltransferase was incubated in the presence of various divalent cations at a room temperature for 5 min. The enzyme activity was determined by the addition of substrate directly to the incubation mixture followed by the standard assay procedure.

Effect of Chemical Modifications on the Enzyme Reaction

To evaluate the possible catalytic role of amino acid residues in the acetylation reaction of this enzyme, several chemical modifications were carried out (Table 4). Yeast acetyltransferase was incubated with each reagent at 30° C. for 15 minutes, dialyzed against 50 mM HEPES buffer, pH 7.4, 150 mM DTT at 4° C. for 3-4 hours. The enzyme activity was determined as described above. The reaction of acetyltransferase with 1 or 5 mM diethyl pyrocarbonate, a histidine-modifying reagent, caused a complete inactivation of the enzyme. The reagents used in Table 4 are: reagents which modify cysteine and cystine residues (NEM, N-ethylmaleimide; IAA, iodoacetic acid; IAM iodoacetamide; pCMB, p-chloromercuribenzoate; DTT, dithiothreitol); reagents which modify HIS, TYR or LYS residues (DEPC, diethyl pyrocarbonate); reagents which modify HIS, TYR or TRP residues (NBS, N-Bromosuccinimide); reagents which modify HIS or carboxyl (Woodward's K; N-ethyl-5-phenylisoxazolium 3'sulfonate); reagents which modify lysine or primary amino acid residues (Succinic anhydride; TNBS, 2,4,6-trinitrobenzenesulfonic acid); reagents which modify TYR residues (N-acetylimidazole); reagents which modify TRP residues (HNBS(CH$_3$)$_2$-Br; dimethyl-(2-hydroxy-5-nitrobenzyl) sulfonium bromide); reagents which modify SER residues (PMSF); and reagents which chelate metal ions (DEAE).

TABLE 4

Effect of Protein Modification Reagents on Enzyme Activity of N-alpha-Acetyltransferase from S. cerevisiae

| Reagent Added | Concentration (mM) | Enzyme Activity (%) |
|---|---|---|
| None | | 100 |
| NEM | 1.0 | 92 |
| | 10.0 | 13 |
| IAA | 1.0 | 100 |
| | 5.0 | 73 |
| IAM | 1.0 | 98 |
| | 10.0 | 63 |
| pCMB | 1.0 | 100 |
| | 10.0 | 55 |
| pCMB + DTT | 1.0 + 10.0 | 100 |
| | 10.0 + 60.0 | 160 |
| DTT | 1.0 | 100 |
| | 10.0 | 110 |
| | 50.0 | 120 |
| DEPC | 0.5 | 52 |
| | 1.0 | 1.6 |
| | 5.0 | 0 |
| DEPC + Hydroxlamine | 1.0 + 250.0 | 0 |
| | 1.0 + 500.0 | 0 |
| NBS | 0.5 | 30 |
| | 5.0 | 0.5 |
| Woodward's K | 1.0 | 79 |
| | 10.0 | 0 |
| Succinic Anhydride | 1.0 | 94 |
| | 10.0 | 71 |
| TNBS | 1.0 | 94 |
| | 10.0 | 76 |
| N-acetylimidazole | 1.0 | 100 |
| | 10.0 | 63 |
| HNBS(CH$_3$)$_2$—Br | 1.0 | 82 |
| | 10.0 | 70 |
| PMSF | 1.0 | 140 |
| | 10.0 | 134 |
| DEAE | 2.5 | 120 |
| | 25.0 | 135 |
| 2-Mercaptoethanol | 10.0 | 110 |

Substrate Specificity

A partial determination of substrate specificity of yeast acetyltransferase was carried out using a substrate containing the first 24 amino acid residues of adrenocorticotropic hormone (ACTH). The amino acid sequences of all ACTH substrates is as described by Lee, F.-J. S., et al. (*J. Biol. Chem.* 263:14948–14955 (1988), which reference has been incorporated by reference herein in its entirety).

Table 5 shows that the acetylation efficiency of the [Phe$^2$] analogue was not significantly different from ACTH (amino acids 1–24). Four truncated forms of ACTH (amino acids 4–10), (amino acids 11–24), (amino acids 7–38) and (amino acids 18–39), lacking different N-terminal residues of ACTH, were not acetylated.

β-Endorphin can be acetylated at N-terminal Tyr residue by rat pituitary acetyltransferase but not by yeast acetyltransferase (Table 6). The substrate specificity using natural substrates in the yeast was further investigated. Yeast alcohol dehydrogenase (ADH) is naturally acetylated at its N-terminal Ser residue. Human superoxide dismutase (SOD) is naturally acetylated at its N-terminal Ala residue and also as expressed as a recombinant protein in yeast. However, endogenous yeast SOD, which is 48% identical to human SOD, is not N-acetylated. Whether or not N-terminal sequence differences between these proteins account for the differences in acetylation remains unclear. As shown in Table 6, synthetic yeast ADH (amino acids 1–24) and synthetic human SOD (amino acids 1–24) can be acetylated by this enzyme. However, yeast ADH already naturally acetylated at its N-terminal Ser residue or synthetic yeast SOD (amino acids 1–24) cannot be acetylated. In addition, yeast enolase containing an Ala residue with a free α-NH$_2$ group is known not to be N-acetylated in vivo and indeed cannot be acetylated by this enzyme. Furthermore, neither calf thymus lysine- or arginine-rich histones could be acetylated by the yeast acetyltransferase.

TABLE 5

RELATIVE ACTIVITY OF YEAST ACETYLTRANSFERASE FOR THE N-ACETYLATION OF ACTH FRAGMENTS

| Substrate | Activity (%) |
|---|---|
| ACTH (1-24) | 100 ± 5 |
| [Phe$^2$]ACTH (1-24) | 90 ± 9 |
| ACTH (4-10) | 0 |
| ACTH (11-24) | 0 |
| ACTH (7-38) | 0 |
| ACTH (18-39) | 0 |

Data reported as mean activity ± SD (N = 3-5).

TABLE 6

RELATIVE ACTIVITY OF YEAST ACETYLTRANSFERASE FOR THE N-ACETYLATION OF VARIOUS SYNTHETIC PEPTIDES AND NATIVE PROTEINS

| Substrate | Activity (%) |
|---|---|
| ACTH (1-24) (Human) | 100 ± 5 |
| β-ENDORPHIN (Human) | 2 ± 2 |
| ALCOHOL DEHYDROGENASE (1-24) (Yeast) | 92 ± 8 |
| ALCOHOL DEHYDROGENASE (Yeast) | 4 ± 2 |
| SUPEROXIDE DISMUTASE (1-24) (Yeast) | 0 |
| SUPEROXIDE DISMUTASE (1-24) (Human) | 86 ± 6 |
| ENOLASE (1-24) (Yeast) | 4 ± 2 |
| HISTONE (lysine-rich) (calf thymus) | 0 |
| HISTONE (arginine-rich) (calf thymus) | 0 |

Data reported as mean activity ± SD (N = 3-5).

Amino Acid Sequences of N$^\alpha$-acetyltransferase

The N$^\alpha$-acetyltransferase was cleaved with trypsin and the fragments were separated on an HPLC phenyl reverse phase column. Peptide fagments (indicated with dashed lines in FIG. 12) were sequenced. The sequence information from two of the sequenced peptide fragments, Fragment 15-3-1 and Fragment 29-1 are as follows:

gly—val—pro—ala—thr—phe—ser—asn—val—lys—pro—leu—tyr—gln—arg    Fragment 15-3-1:

phe—ile—pro—leu—thr—phe—leu—gln—asp—lys—glu—glu—leu—ser—lys  Fragment 29-1:

As detailed below, the sequence information from these two peptide fragments may be used to synthesize oligonucleotide probes as described in Example 2.

III. Genetic Engineering of $N^\alpha$-Acetyltransferase

Sequencing of $N^\alpha$-acetyltransferase

The inventors have completed the molecular cloning and determined the complete cDNA sequence analysis of a eukaryotic $N^\alpha$-acetyltransferase gene. The yeast $N^\alpha$-acetyltransferase protein is encoded by an open reading frame of 2562 bases and consists of 854 amino acids. Its molecular weight calculated from its amino acid composition is 98,575 daltons, and this molecular weight agrees with the subunit $M_r$, estimated to be 95,000±2,000. As described above, the protein sequence analysis of the native protein revealed it to be N-terminally blocked, it is likely that after the cleavage of N-terminal Met residue that the penultimate seryl residue was acylated (possibly acetylated). Although the enzyme is not known to be a glycoprotein, it contains 6 putative N-glycosylation sites (i.e., Asn-X-Ser (or Thr) sequences) at residues 120–122, 161–163, 643–645, 702–704, 761–763, 792–793. The extended, hydrophilic region between residues 508 and 720 is an unusual structural feature of the molecule, although it is not clear whether this region plays a functional role in the regulation or localization of the enzyme. A comparison of the protein sequences of $N^\alpha$-acetyltransferase to other acetyltransferases does not reveal an appreciable percent similarity between them, although certain short sequences have a greater than 50% similarity. These are likely regions where site-specific mutations should be introduced in early attempts to identify residues involved in catalysis.

Taken together, the Northern and Southern blots indicate that there is one gene encoding this $N^\alpha$-acetyltransferase. However, it is not clear whether or not yeast contains still other acetyltransferases capable of modifying the $\alpha$-$NH_2$ group of proteins. Further, previous studies on the substrate specificity of the yeast $N^\alpha$-acetyltransferase have clearly demonstrated that this enzyme is not capable of acetylating $\epsilon$-$NH_2$ groups in peptide substrates or in histones, although a histone-specific acetyltransferase has been demonstrated in yeast (Travis, G. H., J. Biol. Chem. 259:14406–14412 (1984)).

The AAA1 gene is located on chromosome 4 and is positioned immediately adjacent to the 5' flanking sequence of the SIR2 gene. Since SIR2 and three other unlinked SIR gene affect trans repression of the transcription of the HMR and HML genes, which are involved in determining the mating type of haploid yeast, there is no clear-cut relationship between the function of these genes and AAA1.

The yeast AAA1 gene will allow the molecular details of the role $N^\alpha$-acetylation in the sorting and degradation of eukaryotic proteins to be determined.

Cloning of $N^\alpha$-acetyltransferase

This invention further comprises the amino acid sequences of $N^\alpha$-acetyltransferase, the genetic sequences coding for the enzyme, vehicles containing the genetic sequence, hosts transformed therewith, enzyme production by transformed host expression, and utilization of the enzyme in the acetylation of peptides or proteins.

The DNA sequence coding for $N^\alpha$-acetyltransferase may be derived from a variety of sources. For example, mRNA encoded for $N^\alpha$-acetyltransferase may be isolated from the tissues of any species that produces the enzyme, by using the Northern blot method (Alwine et al., Method Enzymol. 68:220–242 (1979)), and labeled oligonucleotide probes. The mRNA may then be converted to cDNA by techniques known to those skilled in the art. The probes may be synthesized based on the known amino acid sequence of $N^\alpha$-acetyltransferase as described above.

Alternately, degenerative DNA probes maybe used to screen a DNA library of a species that produces $N^\alpha$-acetyltransferase, thereby isolating a clone that contains the DNA sequence encoding the enzyme. The DNA library is created by the fragmentation, using one or more restriction endonucleases of the genomic DNA, followed by incorporation into vectors, and use thereof to transform host cells, which are then plated and screened.

The DNA probe may be labeled with a detectable group. Such detectable group can be any material having a detectable physical or chemical property. Such materials have been well-developed in the field of immunoassays and in general most any label useful in such methods can be applied to the present invention. Particularly useful are enzymatically active groups, such as enzymes (see Clin. Chem. 22:1243 (1976)), enzyme substrates (see British Pat. Spec. 1,548,741), coenzymes (see U.S. Pat. Nos. 4,230,797 and 4,238,565) and enzyme inhibitors (see U.S. Pat. No. 4,134,792); fluorescers (see Clin. Chem. 25:353 (1979)); chromophores; luminescers such as chemiluminescers and bioluminescers (see Clin. Chem. 25:512 (1979)); specifically bindable ligands; proximal interacting pairs; and radioisotopes such as $^3H$, $^{35}S$, $^{32}P$, $^{125}I$ and $^{14}C$. Such labels and labeling pairs are detected on the basis of their own physical properties (e.g., fluorescers, chromophores and radioisotopes) or their reactive or binding properties (e.g., enzymes, substrates, coenzymes and inhibitors). For example, a cofactor-labeled probe can be detected by adding the enzyme for which the label is a cofactor and a substrate for the enzyme. For example, one can use an enzyme which acts upon a substrate to generate a product with a measurable physical property. Examples of the latter include, but are not limited to, beta-galactosidase, alkaline phosphatase and peroxidase.

A DNA sequence encoding $N^\alpha$-acetyltransferase may be recombined with vector DNA in accordance with conventional techniques, including blunt-ended or stagger-ended termini for ligation, restriction enzyme digestion to provide appropriate termini, filling in of cohesive ends as appropriate, alkaline phosphatase treatment to avoid undesirable joining, and ligation with appropriate ligases.

To express $N^\alpha$-acetyltransferase transcriptional and translational signals recognized by an appropriate host element are necessary. Eukcaryotic hosts may be mammalian cells capable of culture in vitro, particularly leukocytes, more particularly myeloma cells or other transformed or oncogenic lymphocytes, e.g., EBV-transformed cells. Alternatively, non-mammalian cells may be employed, such as bacteria, fungi, e.g., yeast, filamentous fungi, or the like.

Possible hosts for $N^\alpha$-acetyltransferase, production are mammalian cells, grown in vitro in tissue culture or in vivo in animals. Mammalian cells may provide post-translational modifications to $N^\alpha$-acetyltransferase molecules including correct folding or glycosylation of the correct sites. Mammalian cells which may be useful as hosts include cells of fibroblast origin such as VERO or CHO-K1, or cells of lymphoid origin, such as the hybridoma SP2/O-AG14 or the myeloma P3×63Sgh, and their derivatives. Usually the $N^\alpha$-acetyltransferase construct will be part of a vector having a replication system recognized by the host cell.

In one embodiment, a procaryotic cell is transformed by a plasmid carrying the $N^\alpha$-acetyltransferase-encoded gene. Bacterial hosts of particular interest include *E. coli* K12 strain 294 (ATCC 31446), *E. coli* X1776 (ATCC 31537), *E. coli* W3110 (F−, lambda−, phototropic (ATCC 27325)), and other enterobacterium such as *Salmonella typhimurium* or *Serratia marcescens*, and various Pseudomona species. Under such conditions, the $N^\alpha$-acetyltransferase will not be glycosylated. The procaryotic host must be compatible with the replicon and control sequences in the expression plasmid.

In general, such vectors containing replicon and control sequences which are derived from species compatible with a host cell, are used in connection with the host. The vector ordinarily carries a replicon site, as well as specific genes which are capable of providing phenotypic selection in transformed cells. The expression of the $N^\alpha$-acetyltransferase-encoded DNA can also be placed under control of other regulatory sequences which may be homologous to the organism in its untransformed state. For example, lactose-dependent *E. coli* chromosomal DNA comprises a lactose or lac operon which mediates lactose utilization by elaborating the enzyme $\beta$-galactosidase. The lac control elements may be obtained from bacteriophage lambda plac5, which is infective for *E. coli*. The lac promoter-operator system can be induced by IPTG.

Other promoter/operator systems or portions thereof can be employed as well. For example, colicin E1, galactose, alkaline phosphatase, tryptophan, xylose, tax, and the like can be used.

For a mammalian host, several possible vector systems are available for expression. One class of vectors utilize DNA elements which provide autonomously replicating extra-chromosomal plasmids, derived from animal viruses such as bovine papilloma virus, polyoma virus, adenovirus, or SB40 virus. A second class of vectors relies upon the integration of the desired gene sequences into the host chromosome. Cells which have stably integrated the introduced DNA into their chromosomes may be selected by also introducing one or markets which allow selection of host cells which contain the expression vector. The marker may provide for prototropy to an auxotrophic host, biocide resistance, e.g., antibiotics, or heavy metals, such as copper or the like. The selectable marker gene can either be directly linked to the DNA sequences to be expressed, or introduced into the same cell by co-transformation. Additional elements may also be needed for optimal synthesis of mRNA. These elements may include splice signals, as well as transcription promoters, enhancers, and termination signals. The cDNA expression vectors incorporating such elements include those described by Okayama, H., *Mol. Cel. Biol.* 3:280 (1983), and others.

A wide variety of transcriptional and translational regulatory sequences may be employed, depending on the nature of the host. The transcriptional and translational signals may be derived from viral sources, such as adenovirus, bovine papilloma virus, simian virus, or the like, where the regulatory signals are associated with a particular gene which has a high level of expression. Alternatively, promoters from mammalian expression products, such as actin, collagen, myosin, etc., may be employed. Transcriptional initiation signals may also be selected which allow for repression or activation, so that expression of the genes may be modulated. Of interest are regulatory signals which are temperature-sensitive so that varying the temperature, expression can be repressed or initiated, or are subject to chemical regulation, e.g., metabolite.

Once the vector or DNA sequence containing the constructs has been prepared for expression, the DNA constructs may be introduced to an appropriate host. Various techniques may be employed, such as protoplast fusion, calcium phosphate precipitation, electroporation or other conventional techniques. After the fusion, the cells are grown in media and screened for appropriate activities. Expression of the gene(s) results in production of the $N^\alpha$-acetyltransferase.

The host cells for $N^\alpha$-acetyltransferase production may be immortalized cells, primarily myeloma or lymphoma cells. These cells may be grown in an appropriate nutrient medium in culture flasks or injected into a synergistic host, e.g., mouse or rat, or immunodeficient host or host site, e.g., nude mouse or hamster pouch.

The $N^\alpha$-acetyltransferase of the invention may be isolated and purified in accordance with conventional conditions, such as extraction, precipitation, chromatography, affinity chromatography, electrophoresis, or the like.

IV. Uses of $N^\alpha$-Acetyltransferase $N^\alpha$-acetyltransferase, once produced and purified, can be used, for example, in a pharmaceutical manufacturing environment to N-acetylate a peptide or protein. The N-acetylation is useful in reducing degradation of proteins to be used therapeutically. See the discussion following A. Klibinov, "Unconventional Catalytic Properties of Conventional Enzymes," in *Basic Biology of New Developments in Biotechnology*, pp. 497-518 (A. Hollaender, ed. 1973) On the use of enzymes.

Expression of the $N^\alpha$-acetyltransferase in Plants

Further, the $N^\alpha$-acetyltransferase can be introduced into a plant by genetic engineering techniques to enhance the rate of acetylation. It is known that certain herbicides are inactivated by acetylation. Therefore, it is possible to produce a plant that is more herbicide-tolerant. In thus another embodiment of this invention, the $N^\alpha$-acetyltransferase gene is used to transform a plant to enhance the herbicidal tolerance of the plant.

The coding region for a $N^\alpha$-acetyltransferase gene that may be used in this invention may be homologous or heterologous to the plant cell or plant being transformed. It is necessary, however, that the genetic sequence coding for $N^\alpha$-acetyltransferase be expressed, and produced, as a functional protein or polypeptide in the resulting plant cell. Thus, the invention comprises plants containing either homologous $N^\alpha$-acetyltransferase genes or heterologous $N^\alpha$-acetyltransferase genes that express the enzyme.

In one embodiment of this invention, the $N^{\alpha}$-acetyltransferase comprises a plant $N^{\alpha}$-acetyltransferase that is homologous to the plant to be transformed. In another embodiment of this invention, the $N^{\alpha}$-acetyltransferase comprises an enzyme that is heterologous to the plant to be transformed. Moreover, DNA from both genomic DNA and cDNA encoding a $N^{\alpha}$-acetyltransferase gene may be used in this invention. Further, a $N^{\alpha}$-acetyltransferase gene may be constructed partially of a cDNA clone and partially of a genomic clone. In addition, the DNA coding for the $N^{\alpha}$-acetyltransferase gene may comprise portions from various species.

There are a variety of embodiments encompassed in the broad concept of the invention. In one of its embodiments, this invention comprises chimeric genetic sequences:

(a) a first genetic sequence coding for a $N^{\alpha}$-acetyltransferase that upon expression of the gene in a given plant cell is functional for $N^{\alpha}$-acetyltransferase;

(b) one or more additional genetic sequences operably linked on either side of the $N^{\alpha}$-acetyltransferase coding region. These additional genetic sequences contain sequences for promoter(s) or terminator(s). The plant regulatory sequences may be heterologous or homologous to the host cell.

In a preferred embodiment, the promoter of the $N^{\alpha}$-acetyltransferase gene is used to express the chimeric genetic sequence. Other promoters that may be used in the genetic sequence include nos, ocs, and CaMV promoters. An efficient plant promoter that may be used is an overproducing plant promoter. This promoter in operable linkage with the genetic sequence for $N^{\alpha}$-acetyltransferase should be capable of promoting expression of said $N^{\alpha}$-acetyltransferase such that the transformed plant has increased tolerance to a herbicide. Overproducing plant promoters that may be used in this invention include the promoter of the small subunit (ss) of the ribulose-1,5-biphosphate carboxylase from soybean (Berry-Lowe et al., *J. Molecular and App. Gen.*, 1:483-498 (1982)), and the promoter of the chlorophyll a/b binding protein. These two promoters are known to be light induced in eukaryotic plant cells (see, for example, *Genetic Engineering of Plants, an Agricultural Perspective*, A. Cashmore, Plenum, N.Y. 1983, pages 29-38; Corruzi, G. et al., *J. of Biol. Chem.*, 258: 1399 (1983); and Dunsmuir, P. et al., *J. of Mol. and Applied Genet.*, 2: 285 (1983)).

Further, in another preferred embodiment, the expression of the chimeric genetic sequence comprising the $N^{\alpha}$-acetyltransferase gene is operably linked in correct reading frame with a plant promoter and with a gene secretion signal sequence.

The chimeric genetic sequence comprising a $N^{\alpha}$-acetyltransferase gene operably linked to a plant promoter, and in the preferred embodiment with the secretion signal sequences, can be ligated into a suitable cloning vector. In general, plasmid or viral (bacteriophage) vectors containing replication and control sequences derived from species compatible with the host cell are used. The cloning vector will typically carry a replication origin, as well as specific genes that are capable of providing phenotypic selection markers in transformed host cells, typically resistance to antibiotics. The transforming vectors can be selected by these phenotypic markers after transformation in a host cell.

Host cells that may be used in this invention include prokaryotes, including bacterial hosts such as *E. coli*, *S. typhimurium*, and *Serratia marcescens*. Eukaryotic hosts such as yeast or filamentous fungi may also be used in this invention.

The cloning vector and host cell transformed with the vector are used in this invention typically to increase the copy number of the vector. With an increased copy number, the vectors containing the $N^{\alpha}$-acetyltransferase gene can be isolated and, for example, used to introduce the chimeric genetic sequences into the plant cells. The genetic material contained in the vector can be microinjected directly into plant cells by use of micropipettes to mechanically transfer the recombinant DNA. The genetic material may also be transferred into the plant cell by using polyethylene glycol which forms a precipitation complex with the genetic material that is taken up by the cell. (Paszkowski et al., *EMBO J.* 3:2717-22 (1984)).

In an alternative embodiment of this invention, the $N^{\alpha}$-acetyltransferase gene may be introduced into the plant cells by electroporation. (Fromm et al., "Expression of Genes Transferred into Monocot and Dicot Plant Cells by Electroporation," *Proc. Nat'l. Acad. Sci. U.S.A.* 82:5824 (1985)). In this technique, plant protoplasts are electroporated in the presence of plasmids containing the $N^{\alpha}$-acetyltransferase genetic construct. Electrical impulses of high field strength reversibly permeabilize biomembranes allowing the introduction of the plasmids. Electroporated plant protoplasts reform the cell wall, divide, and form plant callus. Selection of the transformed plant cells with the expressed $N^{\alpha}$-acetyltransferase can be accomplished using the phenotypic markers as described above.

Another method of introducing the $N^{\alpha}$-acetyltransferase gene into plant cells is to infect a plant cell with *Agrobacterium tumefaciens* transformed with the $N^{\alpha}$-acetyltransferase gene. Under appropriate conditions known in the art, the transformed plant cells are grown to form shoots, roots, and develop further into plants. The $N^{\alpha}$-acetyltransferase genetic sequences can be introduced into appropriate plant cells, for example, by means of the Ti plasmid of *Agrobacterium tumefaciens*. The Ti plasmid is transmitted to plant cells on infection by *Agrobacterium tumefaciens* and is stably integrated into the plant genome. (Horsch et al., "Inheritance of Functional Foreign Genes in Plants," *Science* 233:496-498 (1984); Fraley et al., *Proc. Nat'l Acad. Sci. U.S.A.* 80:4803 (1983).)

Ti plasmids contain two regions essential for the production of transformed cells. One of these, named transfer DNA (T DNA), induces tumor formation. The other, termed virulent region, is essential for the formation but not maintenance of tumors. The transfer DNA region, which transfers to the plant genome, can be increased in size by the insertion of the enzyme's genetic sequence without its transferring ability being affected. By removing the tumor-causing genes so that they no longer interfere, the modified Ti plasmid can then be used as a vector for the transfer of the gene constructs of the invention into an appropriate plant cell.

All plant cells which can be transformed by Agrobacterium and whole plants regenerated from the transformed cells can also be transformed according to the invention so to produce transformed whole plants which contain the transferred $N^{\alpha}$-acetyltransferase gene.

There are presently two different ways to transform plant cells with Agrobacterium:

(1) co-cultivation of Agrobacterium with cultured isolated protoplasts, or (2) transforming cells or tissues with Agrobacterium.

Method (1) requires an established culture system that allows culturing protoplasts and plant regeneration from cultured protoplasts.

Method (2) requires (a) that the plant cells or tissues can be transformed by Agrobacterium and (b) that the transformed cells or tissues can be induced to regenerate into whole plants. In the binary system, to have infection, two plasmids are needed: a T-DNA containing plasmid and a vir plasmid.

After transformation of the plant cell or plant, those plant cells or plants transformed by the Ti plasmid so that the enzyme is expressed, can be selected by an appropriate phenotypic marker. These phenotypical markers include, but are not limited to, antibiotic resistance. Other phenotypic markers are known in the art and may be used in this invention.

All plants from which protoplasts can be isolated and cultured to give whole regenerated plants can be transformed by the present invention so that whole plants are recovered which contain the transferred $N^\alpha$-acetyltransferase gene. Some suitable plants include, for example, species from the genera Fragaria, Lotus, Medicago, Onobrychis, Trifolium, Trigonella, Vigna, Citrus, Linum, Geranium, Manicot, Daucus, Arabidopsis, Brassica, Raphanus, Sinapis, Atropa, Capsicum, Datura, Hyoscyamus, Lycopersion, Nicotiana, Solanum, Petunia, Digitalis, Majorana, Cichorium, Helianthus, Lactuca, Bromus, Asparagus, Antirrhinum, Hemerocallis, Nemesia, Pelargonium, Panicum, Pennisetum, Ranunculus, Senecio, Salpiglossis, Cucumis, Browallia, Glycine, Lolium, Zea, Triticum, Sorghum, and Datura.

There is an increasing body of evidence that practically all plants can be regenerated from cultured cells or tissues, including but not limited to all major cereal crop species, sugarcane, sugar beet, cotton, fruit and other trees, legumes and vegetables. Limited knowledge presently exists on whether all of these plants can be transformed by Agrobacterium. Species which are a natural plant host for Agrobacterium may be transformable in vitro. Monocotyledonous plants, and in particular, cereals and grasses, are not natural hosts to Agrobacterium. Attempts to transform them using Agrobacterium have been unsuccessful until recently. (Hooykas-Van Slogteren et al., *Nature* 311:763–764 (1984).) There is growing evidence now that certain monocots can be transformed by Agrobacterium. Using novel experimental approaches that have now become available, cereal and grass species may be transformable.

Additional plant genera that may be transformed by Agrobacterium include Ipomoea, Passiflora, Cyclamen, Malus, Prunus, Rosa, Rubus, Populus, Santalum, Allium, Lilium, Narcissus, Ananas, Arachis, Phaseolus, and Pisum.

Plant regeneration from cultural protoplasts is described in Evans et al., "Protoplast Isolation and Culture," in *Handbook of Plant Cell Culture* 1:124–176 (MacMillan Publishing Co., New York, 1983); M. R. Davey, "Recent Developments in the Culture and Regeneration of Plant Protoplasts," *Protoplasts*, 1983—Lecture Proceedings, pp. 19–29 (Birkhauser, Basel, 1983); P. J. Dale, "Protoplast Culture and Plant Regeneration of Cereals and Other Recalcitrant Crops," in *Protoplasts* 1983—Lecture Proceedings, pp. 31–41 (Birkhauser, Basel, 1983); and H. Binding, "Regeneration of Plants," in *Plant Protoplasts*, pp. 21–37 (CRC Press, Boca Raton, 1985).

Regeneration varies from species to species of plants, but generally a suspension of transformed protoplasts containing multiple copies of the $N^\alpha$-acetyltransferase gene is first provided. Embryo formation can then be induced from the protoplast suspensions, to the stage of ripening and germination as natural embryos. The culture media will generally contain various amino acids and hormones, such as auxin and cytokinins. It is also advantageous to add glutamic acid and proline to the medium, especially for such species as corn and alfalfa. Shoots and roots normally develop simultaneously. Efficient regeneration will depend on the medium, on the genotype, and on the history of the culture. If these three variables are controlled, then regeneration is fully reproducible and repeatable.

The mature plants, grown from the transformed plant cells, are selfed to produce an inbred plant. The inbred plant produces seed containing the gene for the increased $N^\alpha$-acetyltransferase. These seeds can be grown to produce plants that have enhanced rate of acetylation.

The inbreds according to this invention can be used to develop herbicide tolerant hybrids. In this method, a herbicide tolerant inbred line is crossed with another inbred line to produce the hybrid.

Parts obtained from the regenerated plant, such as flowers, seeds, leaves, branches, fruit, and the like are covered by the invention provided that these parts comprise the herbicidal tolerant cells. Progeny and variants, and mutants of the regenerated plants are also included within the scope of this invention.

In diploid plants, typically one parent may be transformed by the $N^\alpha$-acetyltransferase genetic sequence and the other parent is the wild type. After crossing the parents, the first generation hybrids (FI) will show a distribution of $\frac{1}{2}$ $N^\alpha$-acetyltransferase/wild type:$\frac{1}{2}$ $N^\alpha$-acetyltransferase/wild type. These first generation hybrids (FI) are selfed to produce second generation hybrids (F2). The genetic distribution of the F2 hybrids are $\frac{1}{4}$ $N^\alpha$-acetyltransferase/$N^\alpha$-acetyltransferase: $\frac{1}{2}$ $N^\alpha$-acetyltransferase/wild type: $\frac{1}{4}$ wild type/wild type. The F2 hybrids with the genetic makeup of $N^\alpha$-acetyltransferase/$N^\alpha$-acetyltransferase are chosen as the herbicidal tolerant plants.

As used herein, variant describes phenotypic changes that are stable and heritable, including heritable variation that is sexually transmitted to progeny of plants, provided that the variant still comprises a herbicidal tolerant plant through enhanced rate of acetylation. Also, as used herein, mutant describes variation as a result of environmental conditions, such as radiation, or as a result of genetic variation in which a trait is transmitted meiotically according to well-established laws of inheritance. The mutant plant, however, must still exhibit a herbicidal tolerance through enhanced rate of acetylation as according to the invention.

Having now generally described this invention, the same will be better understood by reference to specific examples, which are included herein for purposes of illustration only, and are not intended to be limiting unless otherwise specified.

EXAMPLE 1

Isolation and Purification of $N^\alpha$-Acetyltransferase

Materials and Methods

Enzyme Assays

Enzyme samples of 1-10 μl were added to 1.5 ml Eppendorf tubes containing a reaction mixture of 50 mM Hepes-K+, pH 7.4, 150 mM KCl, 1 mM DTT, 25 μM [$^3$H] acetyl coenzyme A (0.5 μCi, [$^3$H] acetyl coenzyme A from Amersham, unlabeled acetyl coenzyme A from P-L Biochemicals) and 50 μM ACTH (1-24) with a final volume of 100 μl. The assay mixture was incubated at 30° C. for 30 minutes. The reaction was stopped by adding 17 μl 0.5M acetic acid and chilled in an ice bath. The reaction samples were filtrated through 2.5 cm diameter SP membrane (Cuno Inc.) which has been pre-swollen in a wash with 0.5M acetic acid. The membranes were washed three times in 1 ml of 0.5M acetic acid to remove the unreacted [$^3$H] acetyl coenzyme A. The partial dried membranes were counted on a Beckman LS 3801 scintillation counter. The radioactivity in the control represented acetylation of endogenous compounds was subtracted from each sample determination. One unit of activity was defined as 1 pmol of acetyl residues incorporated into ACTH (1-24) under standard assay conditions.

Purification of $N^\alpha$-Acetyltransferase from Yeast Cell Growth and Storage Cells of yeast strain TD 71.8 were grown aerobically at 30° C. in YPD medium (1% yeast extract, 2% Bactopeptone, 2% glucose), harvested at late log phase, and stored at 20° C. with 10% (v/v) glycerol for up to 4 months without loss of activity.

Cell Extract

Cells were thawed and collected by centrifugation at 4000 rpm for 10 minutes (Beckman, JS-4.0 rotor). The cells (800 g, wet weight) were resuspended in 1 liter of buffer A (1M sorbitol, 50 mM Tris-HCl, pH 7.8, 10 mM MgCl$_2$, 3 mM DTT) containing 80 mg of lyticase (Sigma) and the cell suspension was shaken very gently at 30° C. for 45 minutes. All subsequent steps were carried out at 4° C. The spheroplasts were collected by centrifugation at 4000 rpm for 10 minutes, washed by gentle resuspension in 500 ml of Buffer A, collected by centrifugation and resuspended gently in 400 ml of Buffer B (10 mM HEPES-K+, pH 7.4, 1.5 mM MgCl$_2$, 10 mM KCl, and 0.5 mM DTT). The spheroplasts were broken up in this hypotonic buffer by thirty strokes with a glass Dounce homogenizer and 2.0M cold KCl was added to give a final KCl concentration of 0.2M. The homogenate was gently shaken for 30 minutes and debris was removed by centrifugation at 14,000 rpm for 45 minutes (Beckman, JA 14 rotor). The supernatant solution was concentrated by ultrafiltration with PM-30 membrane (Amicon, Lexington, Mass.) and dialyzed overnight against 8 liters of HDG buffer (20 mM HEPES-K+, pH 7.4, 0.5 mM DTT, 10% (v/v) glycerol and 0.02% NaN$_3$) containing 0.2M KCl.

DEAE-Sepharose CL-6B Chromatography

DEAE Sepharose CL-6B (Pharmacia, P-L Biochemicals) was prepared, degassed, and packed into a column (55×2.5 cm) following the manufacturer's recommendation. The column was washed with 4 column volume of HDG buffer containing 0.2M KCl (for 0.2M KCl chromatography) or 50 mM KCl (for linear KCl gradient chromatography). The dialyzed supernatant fluid was loaded onto DEAE Sepharose CL-6B pre-equilibrated in HDG buffer containing 0.2M KCl. Acetyltransferase activity was eluted with same buffer at 24 ml/h. The fractions containing acetyltransferase activity were pooled and concentrated to a volume of 50 ml using a PM-30 ultrafiltration membrane. This concentrated eluate was dialyzed overnight against 4 liters of HDG buffer containing 50 mM KCl and then loaded onto DEAE Sepharose CL-6B pre-equilibrated in HDG buffer containing 50 mM KCl. The column was developed with a linear gradient between 0.05M (250 ml) and 0.5M (250 ml) KCl in HDG buffer at 24 ml/h and fractions containing acetyltransferase activity were pooled and concentrated to a volume of 5 ml.

Hydroxylapatite Chromatography

The concentrated eluate was dialyzed overnight against 4 liters of 0.05M potassium phosphate buffer, pH 7.4, 0.5 mM DTT, 10% (v/v) glycerol, 0.02% NaN$_3$ and applied to hydroxylapatite column (2.5×40 cm) pre-equilibrated with dialysis buffer. The column was developed with a linear gradient between 0.05M (200 ml) and 0.5M (200 ml) potassium phosphate buffer, pH 7.4, each in 0.5 mM DTT, 10% (v/v) glycerol, 0.02% NaN$_3$ and fractions containing acetyltransferase activity were pooled and concentrated to a volume of 2.5 ml.

DE-52 Chromatography

This concentrated elute was dialyzed overnight against 4 liters of HDG buffer containing 50 mM KCl and then loaded onto DE-52 (Whatman) column (2.5×55 cm) pre-equilibrated in HDG buffer containing 50 mM KCl. The column was developed with a linear gradient between 0.05M (250 ml) and 0.5M (250 ml) KCl each in HDG buffer at 24 ml/h and fractions containing acetyltransferase activity were pooled and concentrated to a volume of 1 ml.

Affi-Gel Blue gel Chromatography

This concentrated eluate was dialyzed overnight against 4 liters of HDG buffer containing 50 mM KCl and then loaded onto Affi-Gel Blue gel column (1.5×25 cm) (Bio-Rad) pre-equilibrated in HDG buffer containing 50 mM KCl. The column was developed with a linear gradient between 0.05M (150 ml) and 1M (150 ml) KCl each in HDG buffer at 12 ml/h and fractions containing acetyltransferase activity were pooled and concentrated.

Sodium Dodecyl Sulfate-Polyacrylamide Gel Electrophoresis and Gel Filtration Samples of purified acetyltransferase were loaded onto SDS-8% polyacrylamide gels and subjected to electrophoresis, under reducing conditions, as described by Laemmli, U. K., Nature 227:680–685 (1970). For determination of molecular weight, samples of myosin (205,000), β-galactosidase (116,000), phosphorylase (97,400), bovine albumin (66,000), egg albumin (45,000) and carbonic anhydrase were loaded in parallel lanes. Protein bands were stained with Coomassie Brilliant Blu R in methol-acetic acid. Determination of apparent molecular weight by gel filtration was performed using a Sepharose CL-4B column (2.5×96 cm). The elution buffer was HDG buffer containing 0.2M KCl and the flow rate was 20 ml/h. The elution volume of acetyltransferase was determined by the standard assay and the apparent molecular weight calculated from the relative elution volumes of protein standards including thyroglobulin (669,000), apoferritin (443,000), β-amylase (200,000), alcohol dehydrogenase (150,000), albumin (66,000) and carbonic anhydrase (29,000).

Amino Acid and Protein Sequence Analysis

The amino acid composition was obtained using a Beckman 6300 Amino Acid Analyzer after 24 hr hydrolysis at 110° C. in 6N HCl containing 0.1% phenol. Protein sequence analysis were carried out using an Applied Biosystems 470A Protein Sequencer and an Applied Biosystems 120A Pth Analyzer.

EXAMPLE 2

Molecular Cloning and Sequencing of a cDNA Encoding $N^\alpha$-Acetyltransferase from *Saccharomyces Cerevisiae*

Materials and Methods

Protein Sequence Analysis of $N^\alpha$-acetyltransferase $N^\alpha$-acetyltransferase was purified from yeast as previously described above. $N^\alpha$-acetyltransferase (3 nmoles) was reduced and alkylated, precipitated with cold chloroform/methanol, redissolved in 0.1M $NH_4HCO_3$, incubated with TPCK-treated trypsin (EC 3.4.21.4; Copper Biomedical, Malvern, Pa.) (120 pmol) for 24 hr at 37° C., recovered by lyophilization, and dissolved in 6M guanidine hydrochloride in 0.1% $CF_3COOH$ for HPLC.

Tryptic peptides were separated on a Vydac phenyl (0.46×25 cm) HPLC column, and selected fractions were rechromatographed isocratically once or twice (Wong, W. W., *Proc. Natl. Acad. Sci. USA* 82:7711-7715 (1985)). Chromatographic peaks were detected at 214 and 280 nm, collected manually, and lyophilized. The tryptic peptides were sequenced by automated Edman degradation performed with an Applied Biosystems 470A Protein Sequencer and an Applied Biosystems 120 Pth Analyzer (Moore, S., In: Chemistry and Biology of Peptides, Meienhofer, J. (ed.), Ann Arbor Science, Ann Arbor, Mich., pp. 629-652 (1972)).

Construction and Screening of cDNA Library

Yeast RNA was isolated as described by Sherman et al. (Sherman, F., et al., *Methods in Yeast Genetics*, Cold Spring Harbor Laboratory, Cold Spring Harbor, N.Y. (1986)). Poly(A)+RNA was selected on oligo(dT)-cellulose (Aviv, H., et al., *Proc. Natl. Acad. Sci. USA* 69:1408-1412 (1972)). cDNA was synthesized from 10 μg of poly(A)+RNA by the method of Okayama and Berg (Okayama, H., et al., *Mol. Cell Biol.* 2:161-170 (1982)), as modified by Gubler and Hoffman (Gubler, U., et al., *Gene* 25:263-269 (1983)), except that 10% of second strand was [$^{32}$P]-labeled. The cDNA was prepared for ligation to λgt11 arms using a method introduced by Dr. Brian Seed, Department of Molecular Biology, Massachusetts General Hospital. After the ends of the cDNA were made blunt with T4 DNA polymerase, the cDNA was ligated to adaptors consisting of two oligonucleotides: 3' CTCTAAAG 5' and 5' ACACGAGATTTC 3'. This cDNA was fractionated on a 5 to 20% linear KOAc gradient (5 ml) using a Beckman SW55 rotor centrifuged for 3 hr at 50,000 rpm at 22° C. Fractions (0.5 ml) were collected from the bottom of the tube. The cDNA was precipitated by addition of ethanol and linear polyacrylamide (20 μg/ml). The size of the cDNAs in each fraction was determined on a 1% agarose gel, and the fractions containing cDNAs between 1 and 8 kb were pooled. Ten micrograms of λgt11 DNA (Young, R. A., et al., *Proc. Natl. Acad. Sci. USA* 80:1194-1198 (1983)) was digested with EcoRI and ligated to adaptors (3' GTGTGACCAGATCTCTTAA 5' and 5' CTGGTCTAGAG 3') and precipitated with PEG8000. 600 ng of λgt11 DNA bearing adaptors was ligated to 150 ng of size-selected cDNA bearing complementary adaptors in 2 μl and packaged in vitro (Maniatis, T., et al., *Molecular Cloning: A Laboratory Manual*, Cold Spring Harbor Laboratory, Cold Spring Harbor, N.Y. (1982)) (Stratagene). *Escherichia coli* strain Y1088 was infected with recombinant phage, and the library was amplified once. The recombinant frequency was approximately 82%.

Figure 12A:
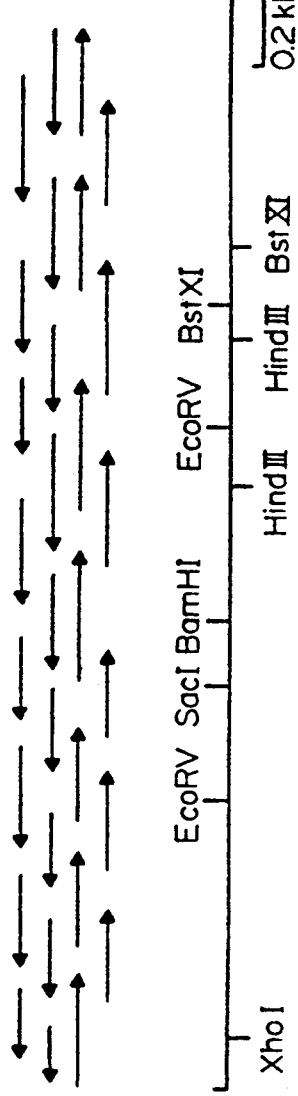
FIG. 12 shows the cloning and sequencing of the cDNA encoding yeast N$^\alpha$-acetyltransferase. (A) shows oligonucleotide probes used for initially screening the λgt11 library. The nucleotide positions indicated by the asterisks differ from the actual DNA sequence shown in (C). The numbering of the tryptic peptides is as follows: the first number refers to the corresponding peak in FIG. 11, the second number refers to the peak in the isocratic HPLC separation (data not shown), and the third number refers to the peak in the second isocratic HPLC separation (data not shown). (B) shows the restriction map and DNA sequencing strategy for the cDNA clones. The arrows indicate the direction and extent of sequence determination for each fragment after exonuclease III deletion. (C) shows the nucleotide and deduced amino acid sequence of N$^\alpha$-acetyltransferase cDNA clones.

Among several peptide sequences, two peptides (peptides 27-3 and 11-3-2; FIG. 12A) were chosen for constructing two oligonucleotide probes (N1 and N2) based on most probable codon usage (Lathe, R., *J. Mol. Biol.* 183:1-12 (1985)). The oligonucleotide probes were synthesized with an Applied Biosystems 380A DNA synthesizer by using the silica-based solid-phase method (Matteucci, M. D., *J. Am. Chem. Soc.* 103:3185-3191 (1981)) and proton-activated nucleoside phosphoramidite method (Beaucage, S. L., *Tetrahedron Lett.* 22:1859-1862 (1981)). The purified oligonucleotide were isolated from the crude synthetic mixtures by PAGE and labeled to a specific activity of $2-8 \times 10^8$ cpm/μg by using [$\gamma$-$^{32}$P]-ATP (New England Nuclear) and T4 polynucleotide kinase (New England Biolabs) (Zoeller, M., et al., *DNA* 3:479-488 (1985)).

In the initial screen, 500,000 recombinant clones in λgt11 yeast cDNA library were plated on *E. coli* Y1088. Duplicate transfers of the clones were made onto nitrocellulose, and the filters were prepared for hybridization (Zoeller, M., et al., *DNA* 3:479-488 (1985)). Afterward, the filters were washed twice at room temperature in 6xSSC (0.15M NaCl/15 mM sodium citrate (NaCl/Cit) containing 0.1% SDS and 0.05% NaPPi), washed once at 5° C. below the minimum $t_d$ (temperature of probe dissociation based on G/C content), and exposed on x-ray film for 2 to 4 days. Maximum and minimum $t_d$ were determined for two pools of redundant oligonucleotide probes (N3 and N4) (Suggs, S. V., et al., In: Developmental Biology Using Purified Genes, Brown, D. (ed.), Academic Press, New York, pp. 683-693 (1981)).

DNA Sequencing and Blot Analysis cDNA fragments were cleaved out from recombinant λgt11 phage DNA by EcoRI digestion. The cDNA fragments were separated by gel electrophoresis in low melting point agarose. The correct DNA band was sliced out, the gel was melted at 65° C., and the DNA was extracted with phenol. The purified cDNA fragments were cloned into the Bluescript plasmid (Stratagene). Both orientations of the complete sequence of the yeast $N^\alpha$-acetyltransferase (AAA1) gene were determined by exonuclease III deletion (Henikoff, S., *Gene* 28:351-359 (1984)), the dideoxy chain termination method of Sanger (Sanger, F., et al., *J. Mol. Biol.* 94:441-448 (1975)) modified for double-stranded sequencing by Guo et al. (Guo, L.-H., et al., *Nucl. Acids Res.* 11:5521-5539 (1983)), and specific priming with synthetic oligonucleotides. All restriction enzymes were purchased from New England Biolabs. RNA and DNA markers were obtained from Bethesda Research Laboratories. Biotrans nylon membrane was from ICN. Poly(A)+RNA was analyzed by Northern blot hybridization (Lehrach, H., *Biochemistry* 16:4743-4751 (1977); Thomas, P. S., *Proc. Natl. Acad. Sci. USA* 77:5201-5202 (1980)). Genomic DNA was isolated from yeast (Sherman, F., et al., *Methods in*, Cold Spring Harbor Laboratory, Cold Spring Harbor, N.Y. (1986)), restriction enzyme digestion, and analyzed by Southern blot hydridization (Southern, E., *J. Mol. Biol.* 98:503-517 (1975)). The chromosome bearing the AAA1 gene was located by hybridizing to a Saccharomyces chromo-dihybridizer (Clonetech) (i.e., a yeast chromosomal blot).

Analysis of Tryptic Peptides of $N^\alpha$-Acetyltransferase

Figure 11:
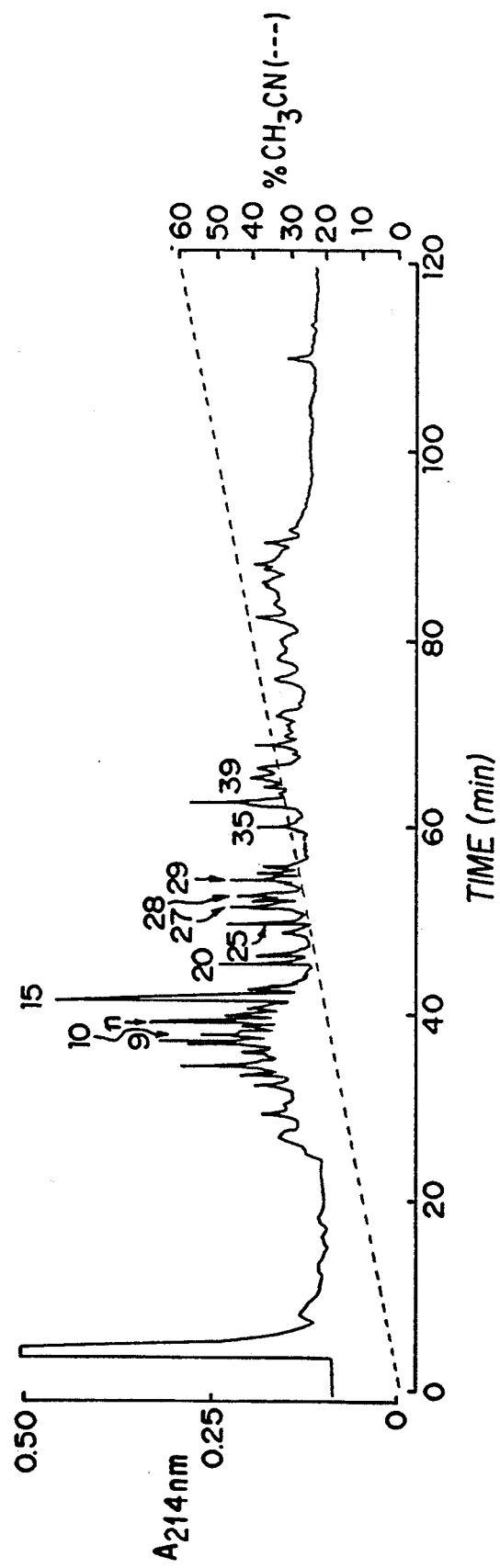
FIG. 11 shows the HPLC separation of yeast N$^\alpha$-acetyltransferase tryptic peptides. Numbers refer to the tryptic peptides, the sequences of which are shown in FIG. 12C.

The method adopted for the identification and cloning of cDNA sequences derived from $N^\alpha$-acetyltransferase mRNA utilized oligonucleotide probes that were constructed based on amino acid sequences of purified $N^\alpha$-acetyltransferase tryptic peptides and on codon usage frequency data (Lathe, R., *J. Mol. Biol.* 183:1-12 (1985)). Tryptic peptides from yeast $N^\alpha$-acetyltransferase were separated by reversed-phase HPLC and collected as 62 pools representing distinct peaks or shoulders (FIG. 11). Three nanomoles of purified $N^\alpha$-acetyltransferase was reduced, alkylated, digested with trypsin, and chromatographed on a 0.46×25 cm Vydac phenyl HPLC column with 0.1% $CF_3COOH$ in a linear gradient of 0-60% $CH_3CN$ over 2 hr. After one or two additional isocratic HPLC separations to resolve further individual sequenceable tryptic peptides (Wong, W. W. et al., *Proc. Natl. Acad. Sci. USA* 82:7711-7715 (1985)), the sequences of 16 peptides, comprising approximately 30% of the entire $N^\alpha$-acetyltransferase molecule were determined.

Synthesis of Oligonucleotide Probes

Two synthetic, codon-usage based oligonucleotides of 57 bases (N1) and 48 bases (N2), corresponding to sequence of a 19-(peptide 27-3) and a 16-residue (peptide 11-3-2) peptide, respectively, were used in the initial screening of the cDNA library (FIG. 12A). In addition, two degenerate oligonucleotide probes of 23 (5' CCXTTGACYTTYTTRCAAGATAA 3') and 20 (3' TCRTCRTGCATYTGRAARTA 5') bases with 64- and 32-fold redundancy, designated N3 and N4, were synthesized based on sequence data for peptides 29-1 and 10-3-1, respectively. The use of four oligonucleotide probes derived from four discrete amino acid sequences allowed the unequivocal identification of the cDNA clones ending $N^\alpha$-acetyltransferase. The protein sequence analyses were completed with repetitive yields between 87% and 93% for 100-200 nmol of each peptide.

Cloning of the Yeast $N^\alpha$-Acetyltransferase cDNA

After initial screening of 500,000 recombinant cDNA clones in the yeast λgt11 cDNA library, eleven clones hybridized to both oligonucleotides N1 and N2. These clones, designated λN1 to λN11, also hybridized with oligonucleotides N3 and N4, and their cDNA inserts were analyzed by restriction enzyme digestions and Southern blot analyses. EcoRI digestion revealed inserts that lacked internal EcoRI sites and ranged from 2.0 to 2.7 kb. The six longest cDNA inserts were subcloned as EcoRI fragments into the Bluescript plasmid, and additional restriction enzyme mapping, Southern blot analyses and nucleotide sequence analyses were carried out. All six cDNA clones (pBN1, pBN3, pBN7, pBN9, pBN10, and pBN11) displayed identical restriction maps (FIG. 12B).

Sequence Analysis of the cDNA Clones

The complete nucleotide sequence, both orientations, of pBN1 was determined using exonuclease III deletions and double-stranded dideoxy chain termination method. The protein sequence translated from the sequence of the 2.71 kb cDNA insert of pBN1 contained identical sequences to those determined from the protein sequence analyses of 16 tryptic peptides (FIG. 12C). However, there was a stop codon located at nucleotides 1409-1411, and the putative reading frame was shifted after this stop codon. Hence, the nucleotide sequences within the corresponding region of the other 5 cDNA clones were determined using synthetic oligonucleotide primers. These 5 clones each contained an additional T which maintained an open reading frame. It is evident that the termination codon in pBN1 was introduced by deletion of a T at nucleotide 1410, presumably resulting from a lack of fidelity for the reverse transcriptase reaction during cDNA synthesis.

The complete nucleotide sequence of the yeast $N^\alpha$-acetyltransferase cDNA is shown in FIG. 12C. The translation initiation site is determined unequivocally, because there is only one ATG codon (nucleotides 22-24), which is preceded by an in-frame termination codon (nucleotides 13-15), located upstream and in-frame with the DNA sequence encoding a tryptic peptide (residues 61-82), which precedes the next methionine in the sequence located at residue 101. There is an open reading frame of 2562 nucleotides encoding the 854 amino acid residues of $N^\alpha$-acetyltransferase, a termination codon (TAG) at nucleotides 2584-2586, and a polyadenylation signal (ATAAAA) located 18 nucleotides upstream from the poly (A) tail.

Comparison of DNA and Protein Sequence Data for Yeast $N^\alpha$-acetyltransferase cDNA with DNA and Protein Sequence Databases The EMBL Nucleic Acid Database revealed an 842-base identity between a 3' region of the cDNA encoding $N^\alpha$-acetyltransferase, beginning at nucleotide 1858 and ending at nucleotide 2699, and the genomic DNA sequence upstream of the 5' end of the SIR2 gene located on chromosome 4 (unpublished data of Shore, D., et al. (Shore, D., et al., *EMBO J.* 3:2817-2823 (1984)) and deposited in the EMBL Nucleic Acid Database). Comparisons between the protein sequence of yeast $N^\alpha$-acetyltransferase and choline acetyltransferase from chicken liver (Deguchi, T., et al., *J. Biol. Chem.* 263:7528-7533 (1988)) revealed a percent similarity of 10%, 12%, 12%, 14%, and 15%, respectively, although there are sequences of 6 to 16 amino acid residues which have percent similarities between 44% and 83% (Devereux, J., et al., *Nucl. Acids Res.* 12:387-395 (1984)).

Northern, Southern, and Chromosomal Blot Analyses

Northern blot analysis of yeast poly(A)+ mRNA using a random-primed [$^{32}P$]-labeled yeast $N^\alpha$-acetyltransferase cDNA probe (pBN1) revealed a 2.7 kb RNA band. Yeast DNA (10 μg) was digested with indicated restriction enzymes. The restriction fragments were electrophoresed in 0.8% agarose in Tris-borate buffer. The DNA was transferred onto a nylon membrane and hybridized with random primed, [$^{32}P$]-AAA1 cDNA (derived from pBN1) for 24 hr and washed (Southern, E., *J. Mol. Biol.* 98:503–517 (1975)).

Southern blot analysis of restriction enzyme digested yeast genomic DNA revealed that the sizes of fragments were similar to the sizes for the restriction fragments of yeast $N^\alpha$-acetyltransferase cDNA (pBN1) (FIG. 12B). Yeast poly(A)+ RNA (10 µg) was electrophoresed on a 1.2% agarose/formaldehyde gel (Maniatis, T., et al., *Molecular Cloning: A Laboratory Manual*, Cold Spring Harbor Laboratory, Cold Spring Harbor, N.Y. (1982)). The mRNA was transferred onto a nylon membrane and hybridized with random primed, $[^{32}P]$-AAA1 cDNA (derived from pBN1) for 24 hr and washed (Lehrach, H., *Biochemistry* 16:4743–4751 (1977); Thomas, P. S., *Proc. Natl. Acad. Sci. USA* 77:5201–5202 (1980)). The gel lane containing the RNA markers was sliced out, visualized by staining with ethidium bromide, and used for determining the molecular size of the yeast poly(A)+ mRNA.

Chromosomal blot analysis with the probe indicates that the yeast $N^\alpha$-acetyltransferase gene (AAA1) is located on chromosome IV. An agarose gel of yeast chromosomal DNA was hybridized with random primed, $[^{32}P]$-AAA1 cDNA (derived from pBN1) for 24 hr and washed according to the manufacturer's recommendations.

Hydrophobicity Profile for Yeast $N^\alpha$-Acetyltransferase

Figure 13:
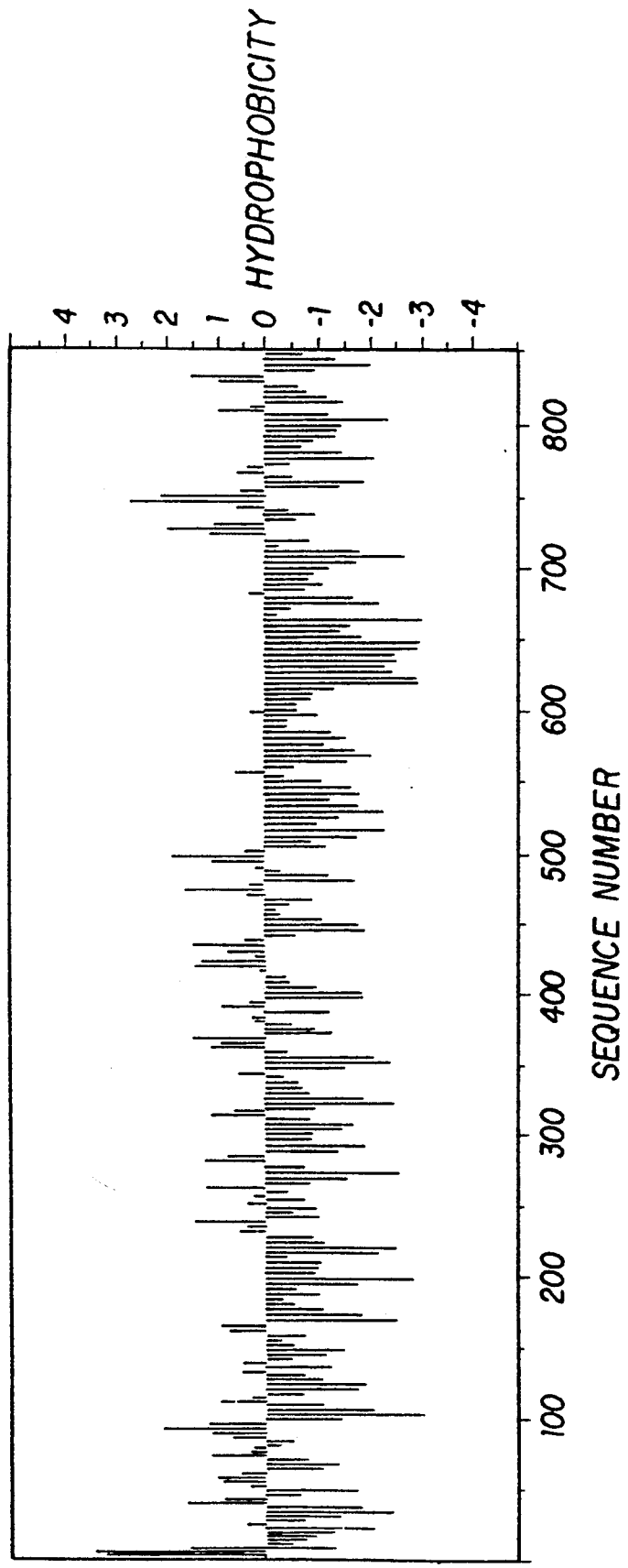
FIG. 13 shows a hydrophobicity plot of yeast N$^\alpha$-acetyltransferase.

The hydrophobicity profile in FIG. 13 was determined using the algorithm of Kyte and Doolittle (Kyte, J., et al., *J. Mol. Biol.* 157:105–132 (1982)) with a window size of 9 (FIG. 13). The protein is rich in charged amino acids, including 96 lysine, 37 arginine, 59 aspartic acid, and 60 glutamic acid residues. In addition, there is an extended hydrophilic region between residues 508 and 720, which is rich in residues associated with $\beta$-turn conformations (Chou, P. Y., et al., In: Peptides: Proceedings of the Fifth American Peptide Symposium, Goodman, M., et al. (eds.), John Wiley and Sons, New York, pp. 284–287 (1977)).

Although the foregoing refers to particular preferred embodiments, it will be understood that the present invention is not so limited. It will occur to those ordinarily skilled in the art that various modifications may be made to the disclosed embodiments and that such modifications are intended to be within the scope of the present invention.

What is claimed is:

1. A recombinant DNA construct consisting essentially of a genetic sequence coding for $N^\alpha$-acetyltransferase having the amino acid sequence as shown in FIG. 12(C).

2. A substantially purified $N^\alpha$acetyltransferase having the amino acid sequence shown in FIG. 12(c).

3. The recombinant DNA construct of claim 1, wherein said construct is selected from the group consisting of cDNA and genomic DNA.

4. A recombinant DNA construct consisting essentially of a genetic sequence coding for $N^\alpha$-acetyltransferase having the amino acid sequence as shown in FIG. 12(C), wherein said genetic sequence is operably linked to translational and/or transcriptional expression signals.

5. The recombinant DNA construct of claim 4, wherein said genetic sequence in said construct is selected from the group consisting of cDNA and genomic DNA.

6. A vector having the recombinant DNA construct of any of claims 1, 3, 4 or 5.

7. The vector of claim 6, wherein said vector is a plasmid.

8. The vector of claim 6, wherein said vector is a bacteriophage.

9. The vector of claim 6, wherein said vector integrates said recombinant DNA construct into a chromosome.

10. A host cell transformed with the vector of claim 6.

11. The host cell of claim 10, wherein said host cell is a eukaryotic cell.

12. The host cell of claim 11, wherein said eukaryotic cell is a yeast cell.

13. The host cell of claim 11, wherein said eukaryotic cell is a mammalian cell.

14. The host cell of claim 10, wherein said host cell is a prokaryotic cell.

15. The host cell of claim 14, wherein said prokaryotic cell is an *E. coli* cell.

16. A substantially purified nucleic acid molecule comprising a genetic sequence coding for $N^\alpha$-acetyltransferase having the amino acid sequence shown in FIG. 12(C), wherein said genetic sequence is selected from the group consisting of RNA and DNA.

17. A recombinant DNA construct comprising a genetic sequence coding for $N^\alpha$-acetyltransferase having the amino acid sequence as shown in FIG. 12(C), wherein said genetic sequence is operably linked to translation and/or transcriptional expression signals.

18. The recombinant DNA construct of claim 17, wherein said genetic sequence in said construct is selected from the group consisting of cDNA and genomic DNA.

19. A vector having the recombinant DNA construct of any of claims 16, 17, or 18.

20. A vector of claim 19, wherein said vector is a plasmid.

21. A vector of claim 19, wherein said vector is a bacteriophage.

22. The vector of claim 19, wherein said vector integrates said recombination DNA construct into a chromosome.

23. A host cell transformed with the vector of claim 19.

24. The host cell of claim 23, wherein said host cell is a eukaryotic cell.

25. The host cell of claim 24, wherein said eukaryotic cell is a yeast cell.

26. The host cell of claim 24, wherein said eukaryotic cell is a mammalian cell.

27. The host cell of claim 23, wherein said host cell is a prokaryotic cell.

28. The host cell of claim 27, wherein said prokaryotic cell is an *E. coli* cell.

* * * * *